US010414696B2

(12) United States Patent
Bryan-Brown et al.

(10) Patent No.: US 10,414,696 B2
(45) Date of Patent: Sep. 17, 2019

(54) BULK MATERIAL COMPOST SYSTEM

(71) Applicant: Green Mountain Technologies, Inc., Bainbridge Island, WA (US)

(72) Inventors: Michael Bryan-Brown, Bainbridge Island, WA (US); Jeffrey P. Gage, Olympia, WA (US)

( * ) Notice: Subject to any disclaimer, the term of this patent is extended or adjusted under 35 U.S.C. 154(b) by 204 days.

(21) Appl. No.: 15/614,241

(22) Filed: Jun. 5, 2017

(65) Prior Publication Data
US 2017/0349502 A1 Dec. 7, 2017

Related U.S. Application Data

(60) Provisional application No. 62/345,713, filed on Jun. 3, 2016, provisional application No. 62/370,147, filed on Aug. 2, 2016.

(51) Int. Cl.
*C05F 17/02* (2006.01)
*C12M 1/16* (2006.01)
(Continued)

(52) U.S. Cl.
CPC ........ *C05F 17/0258* (2013.01); *C05F 17/027* (2013.01); *C12M 21/16* (2013.01);
(Continued)

(58) Field of Classification Search
CPC .... C05F 17/0258; C05F 17/027; C05F 17/02; C12M 27/10; C12M 21/16; C12M 23/00; Y02P 20/145; Y02W 30/43
See application file for complete search history.

(56) References Cited

U.S. PATENT DOCUMENTS

| | | | | |
|---|---|---|---|---|
| 4,134,749 A | * | 1/1979 | Houser et al. | ............ C05F 3/06 71/9 |
| 4,193,873 A | * | 3/1980 | Thrasher | .............. A01K 1/0103 119/450 |

(Continued)

FOREIGN PATENT DOCUMENTS

| | | |
|---|---|---|
| CN | 204509142 U | 7/2015 |
| WO | 03-006400 A1 | 1/2003 |

(Continued)

OTHER PUBLICATIONS

International Search Report and Written Opinion dated Sep. 12, 2017 issued in corresponding International Application No. PCT/US2017/035985, 13 pages.

*Primary Examiner* — Gautam Prakash

(57) ABSTRACT

Methods, apparatus, and system for a compost system to reduce operator time, reduce power utilization, increase intensity of land use by the compost system, increase efficiency of biological activity in bulk material composted by the compost system, reduce odor production by the compost system, and to reuse water applied to and which may leach out of bulk material. The compost system may comprise an aerated pad, a pivot arm attached to a center of the aerated pad, and a control module. The aerated pad may receive a bulk material to be composted into a compost product. The aerated pad may comprise an air nozzle and a drain to direct water from the bulk material to a water collection system. The pivot arm may deposit the bulk material on the aerated pad. The control module may manage a temperature inside the bulk material using the air nozzle.

26 Claims, 26 Drawing Sheets

(51) Int. Cl.
*C12M 3/04* (2006.01)
*C12M 1/00* (2006.01)

(52) U.S. Cl.
CPC ............ *C12M 27/10* (2013.01); *C05F 17/02* (2013.01); *C12M 23/00* (2013.01); *Y02P 20/145* (2015.11); *Y02W 30/43* (2015.05)

(56) References Cited

U.S. PATENT DOCUMENTS

| | | | | | |
|---|---|---|---|---|---|
| 4,326,874 | A | * | 4/1982 | Burklin | ............... C05F 17/0072 435/290.4 |
| 4,448,690 | A | * | 5/1984 | Maphis | ................... C02F 3/046 111/125 |
| 4,869,877 | A | * | 9/1989 | Sellew et al. | ....... C05F 17/0235 435/290.2 |
| 5,102,803 | A | * | 4/1992 | Weaver | ............... C05F 17/0072 261/87 |
| 5,269,634 | A | * | 12/1993 | Chynoweth et al. | ..... B09B 1/00 405/129.25 |
| 5,459,071 | A | * | 10/1995 | Finn | .................... C05F 17/0235 366/345 |
| 5,586,731 | A | * | 12/1996 | Glaze et al. | .............. B01F 3/06 172/119 |
| 6,099,613 | A | * | 8/2000 | Allen et al. | ......... C05F 17/0054 71/9 |
| 6,284,529 | B1 | * | 9/2001 | Carrera | ............... C05F 17/0235 435/290.2 |
| 8,048,668 | B1 | | 11/2011 | Mathsen et al. | |
| 2010/0184131 | A1 | * | 7/2010 | Nicoletti et al. | ........ C02F 11/18 435/41 |

FOREIGN PATENT DOCUMENTS

WO 2010-042700 A2 4/2010
WO 2011-152997 A1 12/2011

* cited by examiner

BULK MATERIAL COMPOST SYSTEM

CROSS-REFERENCE TO RELATED APPLICATIONS

For all purposes, this application claims the benefit of the filing dates of and incorporates by reference U.S. provisional patent application Ser. No. 62/345,713, filed on Jun. 3, 2016, and U.S. provisional patent application Ser. No. 62/370,147, filed on Aug. 2, 2016.

FIELD

The present disclosure relates to a system to compost organic materials.

BACKGROUND

Efficient handling of bulk materials or compost materials (the terms "bulk materials" and "compost materials" may be used interchangeably herein) is essential for economic operation of a large scale compost facility. However, design of large scale compost facilities often assumes significant labor and energy inputs to handle bulk materials, which can make economic operation problematic. A significant amount of operator labor is often required to move processing equipment—such as loaders, grinders, turners and screeners—to bulk material piles, front end loaders and operator labor are required to move bulk material piles to the processing equipment, and operator labor and front end loaders may be required to place odor-containing covers on top of bulk material piles.

Front end loaders increase the capital cost of material handling and require labor input. Front end loaders also can compact bulk materials; compaction of bulk material may impair biologic composting activity. Windrow turners improve agitation compared to front end loaders but may not aerate a compost pile, may require traveling lanes through or between compost piles, require operator labor, and cannot be used for may operations, such as placement of covers. Traveling lanes may substantially increase land area required to operate a compost facility.

Aerated static piles comprise air pipes beneath piles of bulk material. Aerated static piles improve space efficiency and may provide continuous aeration. However, aerated static piles often are compacted due to the action of front end loaders. Placement and removal of aeration pipes beneath a pile of bulk material can be labor intensive, difficult, and/or cumbersome.

A layer of fibrous material, tarps, or other material may be placed on top of aerated piles to control the release of odors. Placement of such material is often accomplished by driving front end loaders onto piles, though this can result in compaction. Biofilters may be used to treat air that is suctioned from aerated composting piles to reduce odors. However, biofilters take up significant area and maintenance may be required to maintain moisture levels within the pile and within the biofilter.

Most composting facilities cannot discharge untreated stormwater or leachate, so retention ponds with aeration treatment systems are used. These systems take up even more processing space and may require containment for odors as well as fencing to reduce accidental drownings and/or incursion by animals.

Figure 1:
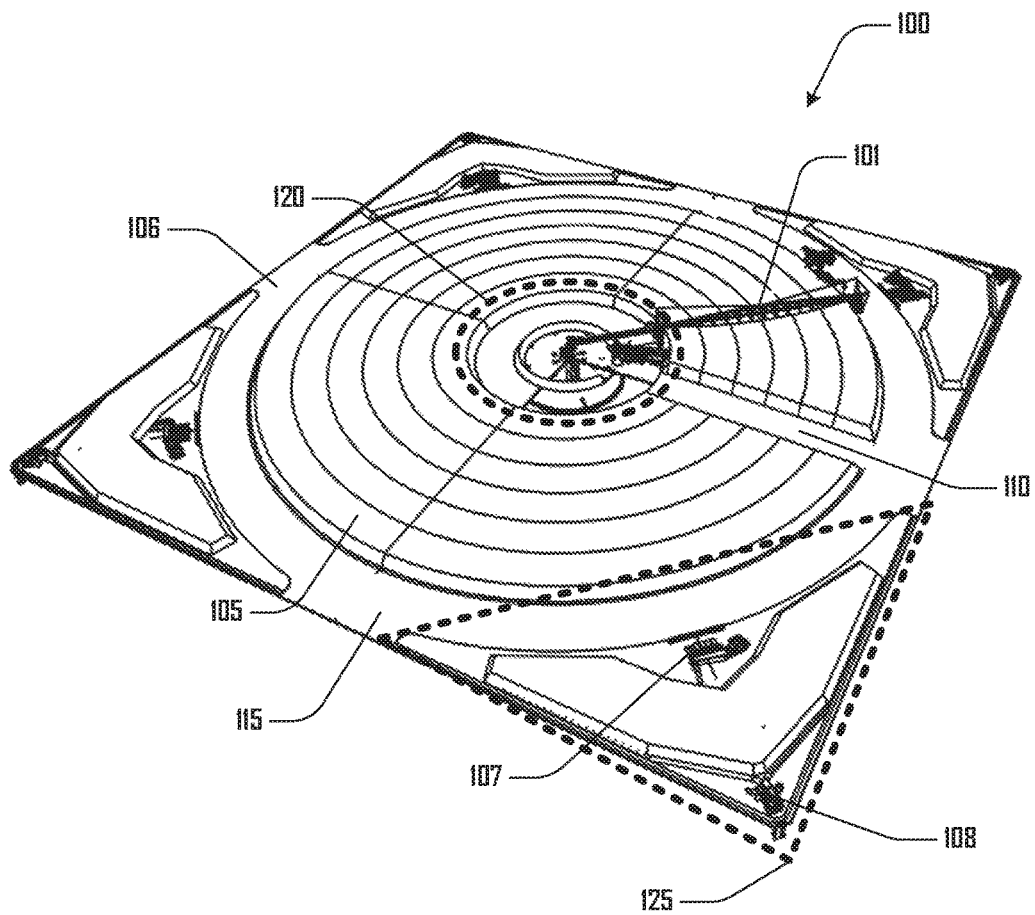
FIG. 1 illustrates an example of an embodiment of a site layout for a compost system.

Although the following Detailed Description will proceed with reference being made to illustrative embodiments, many alternatives, modifications, and variations thereof will be apparent to those skilled in the art.

DETAILED DESCRIPTION

Following are defined terms in this document.

As used herein, "concentric", "coaxial", and "coaxial" refer to two or more objects that share a center or axis. Circles and spirals may be concentric.

As used herein, "radial" refers to an object, unit, or the like that appears to radiate from a point. Spokes of a wheel form a radial pattern.

As used herein, "bulk material" and "compost material" refers to an agglomeration of material comprising at least a subset that may be decomposed by activity of biologic organisms. Bulk material may also comprise material that is not generally be decomposed by activity of biological organisms, such as rocks, metals, plastics (all of which may decompose, including by activity of biological organisms, but generally over a long period of time or under other than typical ambient atmospheric conditions).

As used herein, "biocover" refers to a material placed on the surface of a bulk material for a purpose, such as to consume methane, volatile organic compounds and odors, reduce evaporation, provide protection from sunlight, provide insulation, or the like. Examples include straw, grass, dehydrated sewage sludge, wood fibers, large "overs" or woody fractions screened from bulk material, cellulose fiber, with or without a hydrocolloid, and porous or "breathable" fabrics, tarps, or films.

As used herein, "biochemical oxygen demand" and "biological oxygen demand" (BOD) refer to an amount of dissolved oxygen needed by aerobic biological organisms to break down organic material in a water sample at a temperature over a period of time.

In overview, disclosed is a compost system to reduce operator time, reduce power utilization, increase intensity of land use by the compost system, increase efficiency of biological activity in bulk material composted by the compost system, reduce odor production by the compost system, and to reuse water applied to and which may leach out of bulk material.

The compost system may comprise a pivot arm and an aerated pad. The pivot arm may be attached to a pivot at the center of the aerated pad. The pivot may allow the pivot arm to rotate around the aerated pad. The pivot arm may be extendable and retractable. The pivot arm may deposit bulk material on the aerated pad. The pivot arm may deposit a biocover on the bulk material. The pivot arm may comprise a water outlet (or sprinkler or sprayer) to spray water and/or an aqueous biocover onto the bulk material. The water outlet may spray onto an area where bulk material has been deposited on, is being deposited onto, or is being turned over on the aerated pad. The water outlet may apply water at the discharge end of the pivot arm so as to avoid wetting a conveyor belt of the pivot arm.

The pivot arm may comprise one or more of a ground drive system, a conveyor belt, a power outlet, an air duct, an air knife and/or air vacuum, a rotary bulk material distributor or flail, a position sensor to detect a position of the pivot arm and/or a compost handling equipment, a depth sensor to detect a depth of bulk material on the aerated pad, and a carriage to be secured to the compost handling equipment.

The conveyor belt may convey at least one of a bulk material or a biocover. The conveyor belt may comprise more than one conveyor belt, wherein one of the conveyor belts may extend. In combination with the ground drive system, the extendable conveyor belt may allow the pivot arm to deposit bulk material in a range of circular patterns on the aerated pad.

The carriage may be mobile along the pivot arm. The carriage may comprise a conduit to convey power, water, and/or data to/from the compost handling equipment.

The compost handling equipment may be mobile relative to the pivot arm and/or relative to deposited bulk material. The compost handling equipment and carriage may be attached via a tether which allows the compost handling equipment mobility while providing the compost handling equipment with services, such as power, water, data, hydraulic fluid, or the like. The compost handling equipment may be one of a mobile compost turner, a grinder, an air knife and vacuum, a loader, and/or a screener. The compost handling equipment may comprise one or more sensors, such as to detect a position or orientation of the compost handling equipment, a depth of bulk material, a moisture content of bulk material, a temperature of bulk material, air, or water, a status of the compost handling equipment, or the like. Sensors in the compost handling equipment may transmit information to the control module.

The mobile compost turner may turn over the bulk material. The mobile compost turner may transport the bulk material toward the center of the pivot arm. The mobile compost turner may transport the bulk material toward the center of the pivot arm as it turns over the bulk material. The mobile compost turner may turn over the bulk material in concentric windrows, relative to the center of the pivot arm. The concentric windrows may follow an arc, including a portion of an arc, of a circle or spiral. The mobile compost turner may turn over the bulk material in radial windrows, relative to the center of the pivot arm.

The air knife and vacuum may separate relatively low density components from bulk material, such as plastic.

The compost system may comprise an air handling system. The air handling system may collect air from different locations of the compost system. For example, the air handling system may collect air from at least one of i) a location proximate to active deposition of bulk material on the aerated pad, ii) a location proximate to active turning over of the bulk material, iii) a water catchment vessel, and/or iv) air nozzles used to inject air into or to withdraw air from the bulk material. The air handling system may comprise one or more air filters. The air filters may comprise a porous solid media with a high surface area, wherein the high surface area is to contact the volume of air, a volume of water, wherein the volume of air is to be bubbled through the volume of water, and/or a cyclotron separator. The air handling system may comprise sensors such as thermometers, humidity sensors, pressure sensors, airflow sensors, and the like.

The compost system may comprise a water collection system. The water collection system may comprise or be referred to as a water treatment system. The water collection system may comprise one or more catchment vessels to catch water from the bulk material (such water may also be referred to herein as "leachate"). The catchment vessels may comprise one or more peripheral catchment vessels and/or central catchment vessels. The peripheral catchment vessel may be located in at least one corner of a rectangle, wherein the rectangle surrounds a circular area where bulk material is deposited on the aerated pad. The peripheral catchment vessel may drain or otherwise feed water to the central catchment vessel. The catchment vessels may precipitate and decompose biologic material in leachate.

Air from the air handling system may be pumped or "bubbled" into leachate in the catchment vessels. Air bubbled may be bubbled into a catchment vessel to reduce dust and contaminants, to change a temperature of air in the air handling system, to change a humidity level in the air, and the like.

Leachate may be applied to bulk material; leachate may be applied to bulk material after a desired BOD is obtained in the leachate.

Catchment vessels may comprise a floating dock and an air plenum below the floating dock. The floating dock may comprise an air filter. The air filter may be a porous media with a high surface area, wherein the high surface area is to contact a volume of air. The volume of air may be provided by or pushed through the air filter by the air handling system. The air filter may be biologically active. The volume of air may be calculated to pass through the air filter over a period of time to achieve a result. The result may be to reduce an odor in the volume of air and/or may modify a temperature and/or a moisture content of the volume of air.

The aerated pad may be concrete. The aerated pad may comprise a drain, to drain leachate to a catchment vessel. The aerated pad may comprise a sloped top surface. The sloped top surface may slope in at least one of the following directions: toward the center of the aerated pad, away from the center of the aerated pad, and/or toward a corner of a site. Drains may be located at a low point of the sloped top surface.

The aerated pad may comprise air nozzles. The air nozzles may be below-grade, relative to a top surface of the aerated pad. The air nozzles may be self-cleaning. An air pressurization system may provide positive or negative air pressure to the air nozzles. The air pressurization system may be a component of the air handling system. A control module may direct the air pressurization system to provide the positive or negative air pressure in response to one or more of a temperature inside the bulk material, a temperature of air in the air pressurization system, a temperature of air above the bulk material, a biologic activity of the bulk material, an age of a portion of the bulk material, or a moisture content of the bulk material and/or of the air.

The air nozzles may comprise a first pipe attached to a main air manifold, a second pipe sized to fit around or inside of the first pipe, an air orifice to fit inside of or over the second pipe, a securement fixture to secure the first and second pipes in a desired relative position when the aerated pad is poured, and a variable spacer to position the air orifice at a height relative to a surface of the aerated pad. The variable spacer may have a variable height, allow the air orifice to be re-positioned at a height relative to a surface of the aerated pad.

Operation of the compost handling equipment, pivot arm, air handling system, and water collection system may be "automatic"; as used herein, "automatic" describes that components may be controlled by a control module. The control module may comprise a computer, sensors, and actuators. The sensors may be sensors of or in the compost handling equipment, pivot arm, air handling system, and water collection system, which sensors may transmit information to the computer. The actuators may be motors, solenoids, valves, and the like in or of the compost handling equipment, pivot arm, air handling system, and water collection system. The actuators may be controlled by the computer.

FIG. 1 illustrates an example of a Site 100 for a compost system. In this example of Site 100, a pile of bulk material is arranged in a circular configuration around a center of Site 100, much like a wheel. Such bulk material may be referred to herein as a "Bulk Material Wheel 105". Bulk Material Wheel 105 may be, for example, 5 to 15 feet in depth. A perimeter of Site 100 is illustrated in FIG. 1 as a square (with sides of equal length), though may be a rectangle or other shape. As discussed further herein, the bulk material may be deposited in Bulk Material Wheel 105 by front end loaders and/or a pivot arm extending over Bulk Material Wheel 105, such as Pivot Arm 101 (embodiments of pivot arms are discussed at greater length, herein). As discussed further herein the Bulk Material Wheel 105 may be present on a pad, such as Pad 106. Pad 106 may be concrete, dirt, or another material. As discussed further herein, Pad 106 may comprise air nozzles to inject air into and/or withdraw air from Bulk Material Wheel 105.

As it dries and degrades, the bulk material in Bulk Material Wheel 105 may be moved from the outside toward the center of Bulk Material Wheel 105 by turning and moving equipment. As it is moved toward the center, the bulk material may be turned over. The circular design reduces land area requirements and maintains consistent pile depth as the bulk material dries and degrades.

An access road or keyway (referred to herein as "Keyway 110") may be cut, left, or otherwise formed through or in Bulk Material Wheel 105 to allow for access to a Center Area 120 of Bulk Material Wheel 105. Keyway 110 and Center Area 120 may be used, for example, to remove finished, composted, bulk material product, such as by truck, and/or to allow access to or by service equipment and components in Center Area 120 and along Keyway 110.

A Circular Road 115 may be located on a perimeter of Bulk Material Wheel 105 to facilitate service of equipment, to place fresh bulk material on the perimeter of Bulk Material Wheel 105 and the like. This may avoid unnecessary handling of bulk material by front end loader and may improve processing efficiency.

Connections for power, air, water, data, and other utilities may be located at a center of Site 100, enabling one or reduced utility connection point(s) for equipment which uses such services.

Using an arc layout such as Bulk Material Wheel 105 provides advantages in comparison to a linear layout typical of legacy aerated composting systems. For example, the curve allows a conveyor with a fixed pivot end, such as Pivot Arm 101, to load compost material onto a pad without the use of front end loaders. Bulk material may be conveyed and loaded directly from other processing equipment without re-handling with a loader. The curved layout reduces the working area required to be covered with concrete which reduces construction costs, surface area requiring storm water collection and distance traveled by front end loader when unloading compost from the zones. The Bulk Material Wheel 105 can extend up to 330 degrees or more of a full circle, leaving a small arc segment such as Keyway 110, to access a loading hopper of the Pivot Arm 101.

Site 100 may be located inside a building, roof, or may be open to the environment depending on local weather conditions, land use requirements, and the like. Site 100 and components thereof may be constructed, for example, using concrete, reinforced concrete, composite materials, plastic, and the like.

Figure 2:
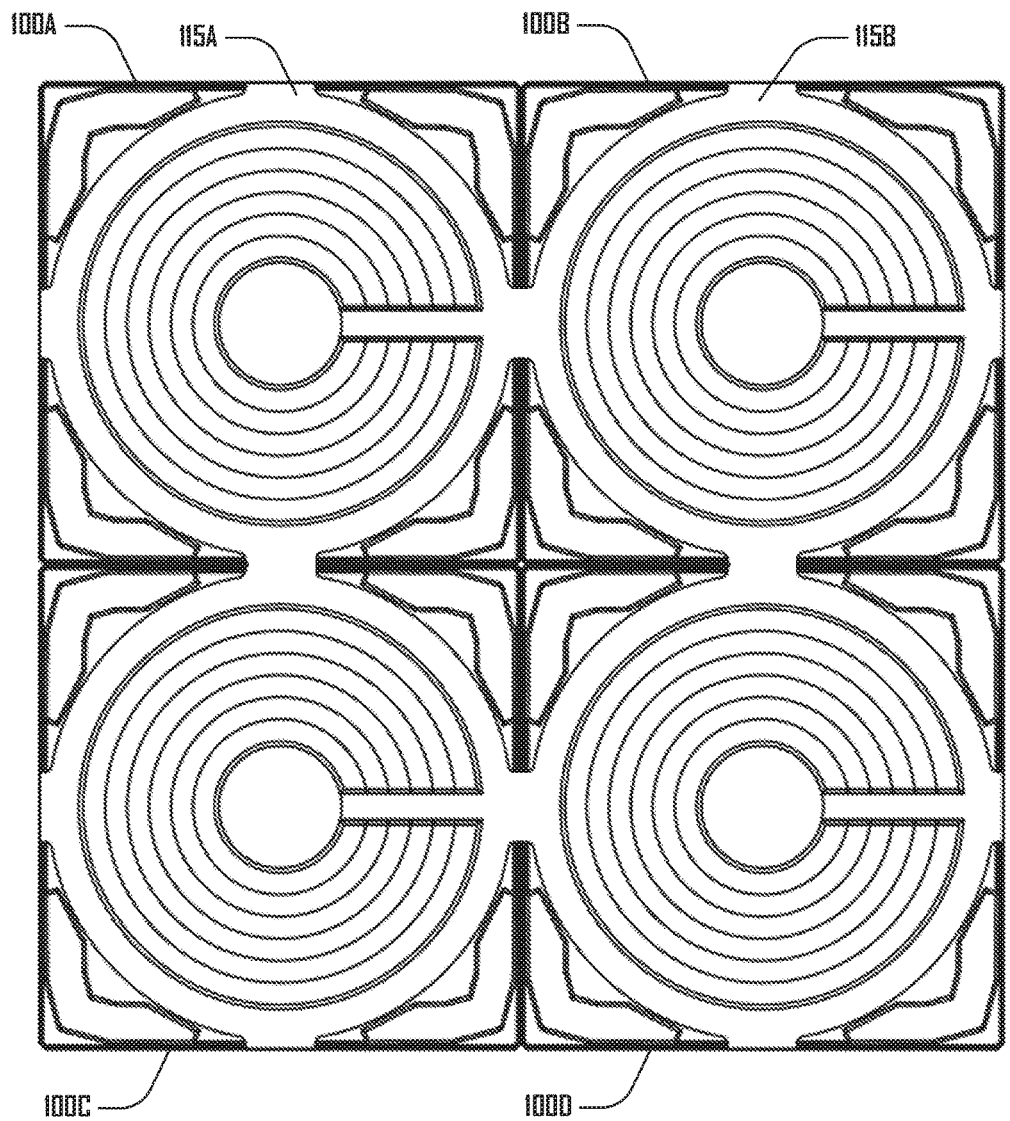
FIG. 2 illustrates an example of an embodiment of multiple adjoining compost system sites.

More than one Site 100 may be connected, for example, such as Site 100A, Site 100B, Site 100C, and Site 100D illustrated in FIG. 2. A first Circular Road 115A in or of a first Site 100A may be used to access a second or other Circular Road 115B in or of a second Site 100B.

Figure 3:
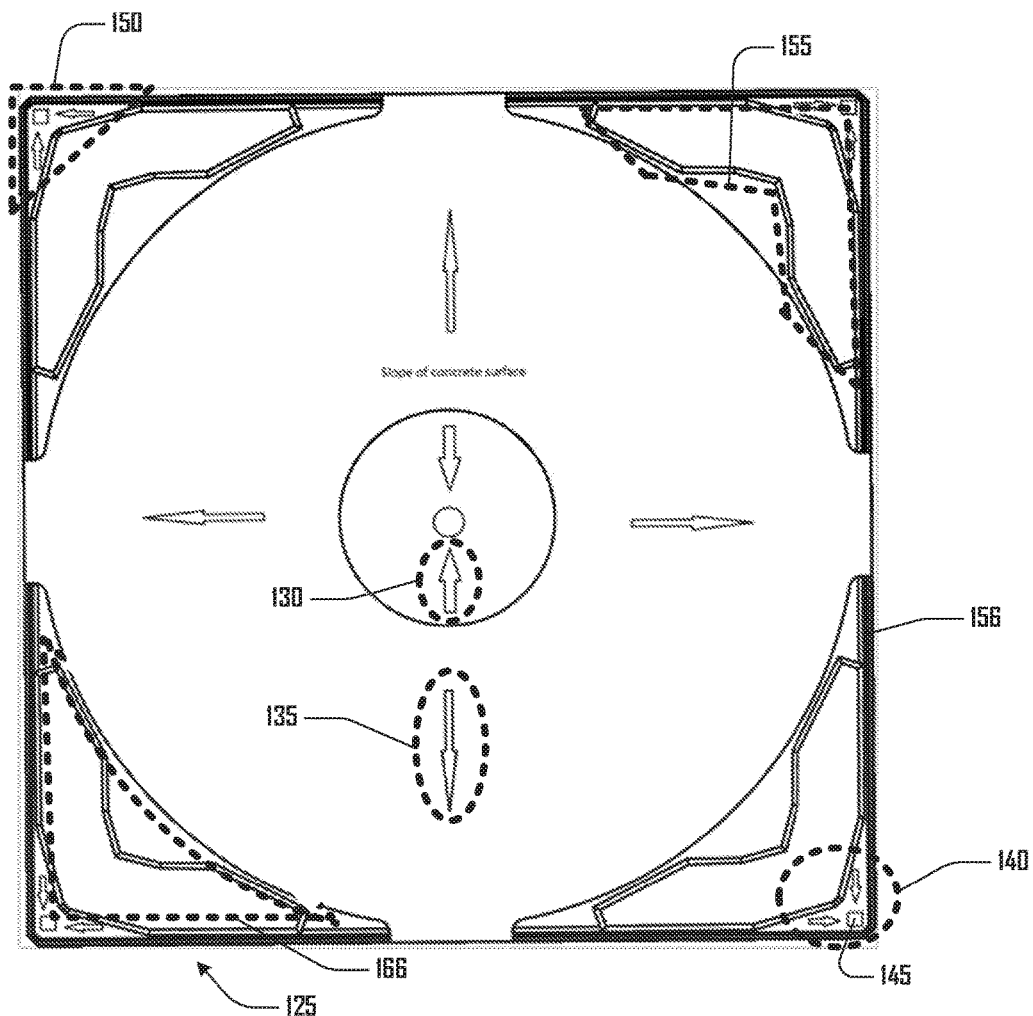
FIG. 3 illustrates an example of an embodiment of a compost system site, with drainage and other elements highlighted.

Areas outside of Circular Road 115 that transition Site 100 from round to rectangular are collectively referred to herein as "Corners 125" (or individually, as a "Corner 125"). Corners 125 may be low points for collecting surface and drainage water. Slopes may be provided in Site 100 for drainage. For example, arrows in FIG. 3 illustrate examples of Center Slope 130 in Center Area 120, Wheel Slope 135 below Bulk Material Wheel 105, and Corner Slope 140. Such slopes may be built into Site 100. Center Slope 130 may channel water falling in Center Area 120 to a central drain. Wheel Slope 135 may channel water to Corner Slopes 140.

Referring to FIG. 3, one or more Corner Drain(s) 145, such as in each Corner 125, may drain water from Bulk Material Wheel 105. Bioswales 150 in or on Corners 125 may be used to pretreat process and drainage water. Bioswales 150 may comprise landscape elements to concentrate, filter, and remove silt and pollution from surface runoff water. They may comprise a swaled drainage course, such as Bioswale Trench 156, with gently sloped sides (such as less than 6%) and may have vegetation, compost, and/or riprap. The slopes and composition of Bioswales 150 and Bioswale Trench 156 may be designed to hold water in the swale drainage for a desired period of time.

Figure 4:
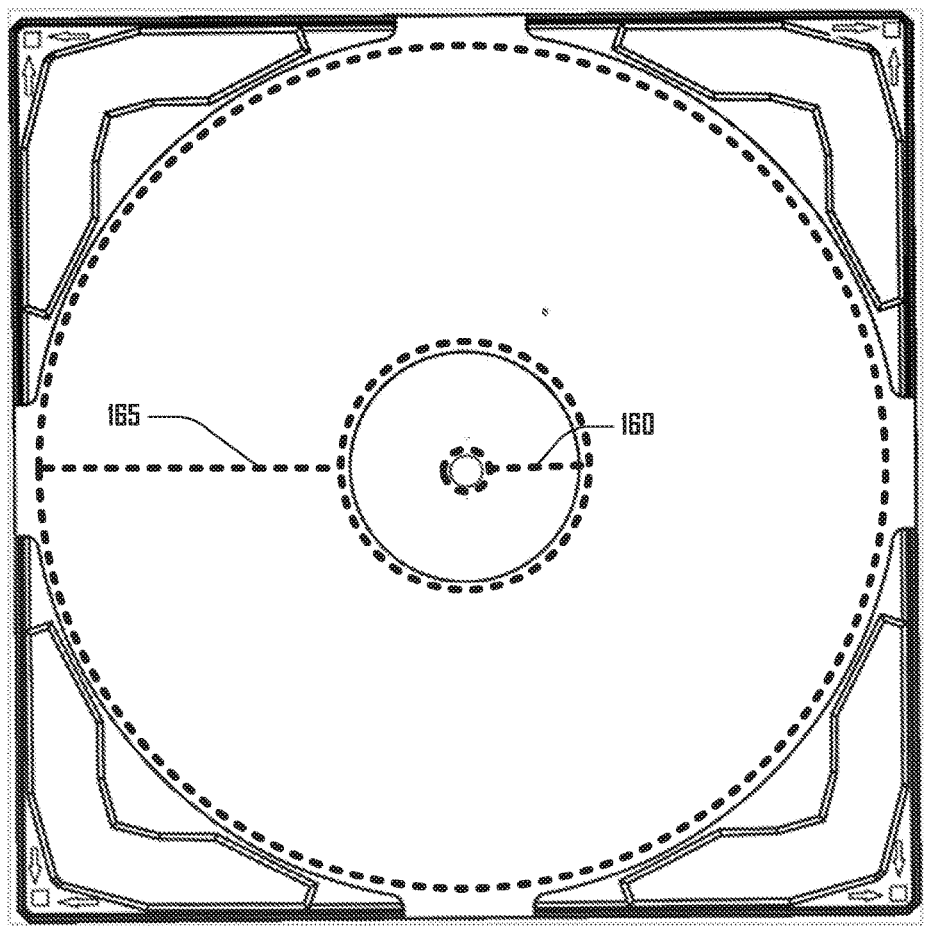
FIG. 4 illustrates an example of an embodiment of a compost system site, with some water catchment vessels highlighted.

Water may transfer, such as via Corner Drain 145, into one or more water catchment vessels. Referring to FIG. 3, a first water catchment vessel may be below grade of Corner 125, in Corner Vault 166, which may occupy some or all of a corner of Site 100, extending below grade (Corner Vault 166 may also be referred to herein as a "peripheral catchment vessel"). Referring to FIG. 4, additional water catchment vessels may also comprise, for example, Holding Tank 165 and Center Collection Vault 160. Catchment vessels may comprise sensors, such as water level sensors and/or BOD sensors.

Figure 5:
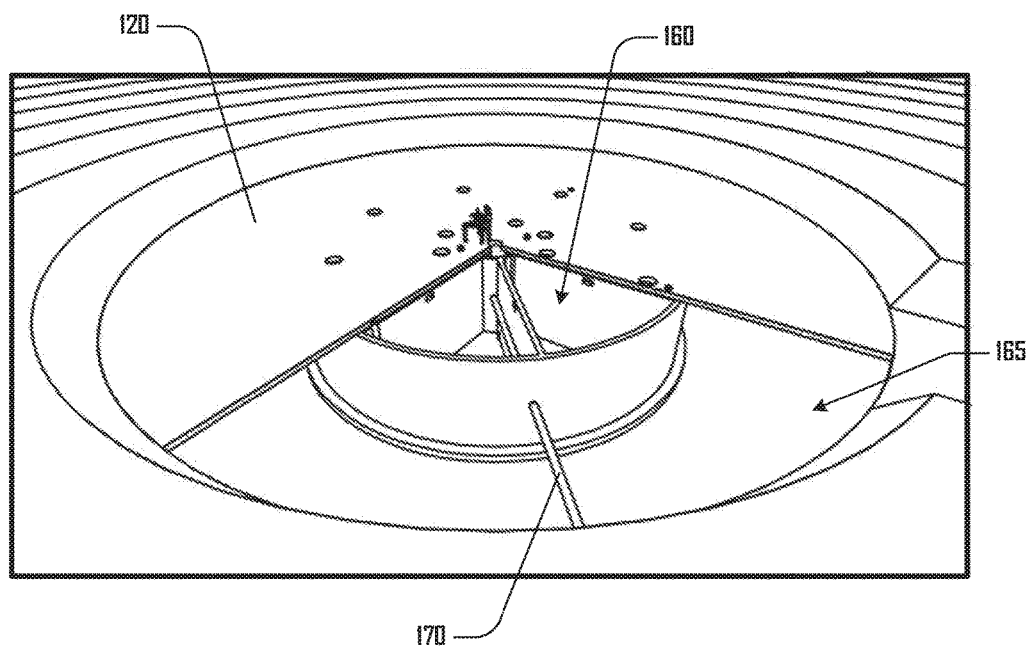
FIG. 5 illustrates an example of an embodiment of a compost system site, with some water catchment vessels and other components highlighted.

Transfer of water into catchment vessels may be by gravity, such as via sloped surfaces of Site 100, and/or through the use of pumps. Referring to FIG. 5, and by way of example, Corner Drain Pipe 170 may transfer water to Center Collection Vault 160 though gravity. Water in Center Collection Vault 160 may be pumped into Holding Tank 165. Referring to FIG. 1, Pump 107 and/or Pump 108 may be water pumps.

Holding Tank 165, Center Collection Vault 160, and/or Corner Vault 166 may be divided into sections or chambers, to allow separate aeration and settling of solids in each section or chamber. Water from a water catchment vessel may be pumped into or sprayed onto bulk material, such as onto Bulk Material Wheel 105, to maintain desired moisture content in the bulk material.

In composting facilities, significant odor may be produced by surface and process water, which may develop anaerobic conditions with high BOD. To maintain aerobic conditions in water catchment vessels, to remediate odors, to change a temperature of water and/or air, and/or to reduce dust in collected air, air may be bubbled into one or more of water catchment vessels. As discussed further herein, air bubbled into the water catchment vessels may originate from an air handling system. An air handling system may collect air above Bulk Material Wheel 105, such as from vacuums located above where bulk material is being deposited in Bulk Material Wheel 105, where bulk material in Bulk Material Wheel 105 is being turned over, and from air nozzles located below Bulk Material Wheel 105. Air pumps to collect air and/or bubble air into water catchment vessels may be located, for example, in the corners of Site 100, in Center Area 120, or in other available space. For example, referring to FIG. 1, Pump 107 and/or Pump 108 may be air pumps.

To filter air discharged into a water catchment vessel, Biofilters 155 may be in or on top of such water catchment vessels. For example, in FIG. 3 and other of the Figures, Corner Vault 166 is illustrated as comprising Biofilters 155. Biofilters 155 may be used to remove odors from air pushed through water catchment vessels.

Figure 6:
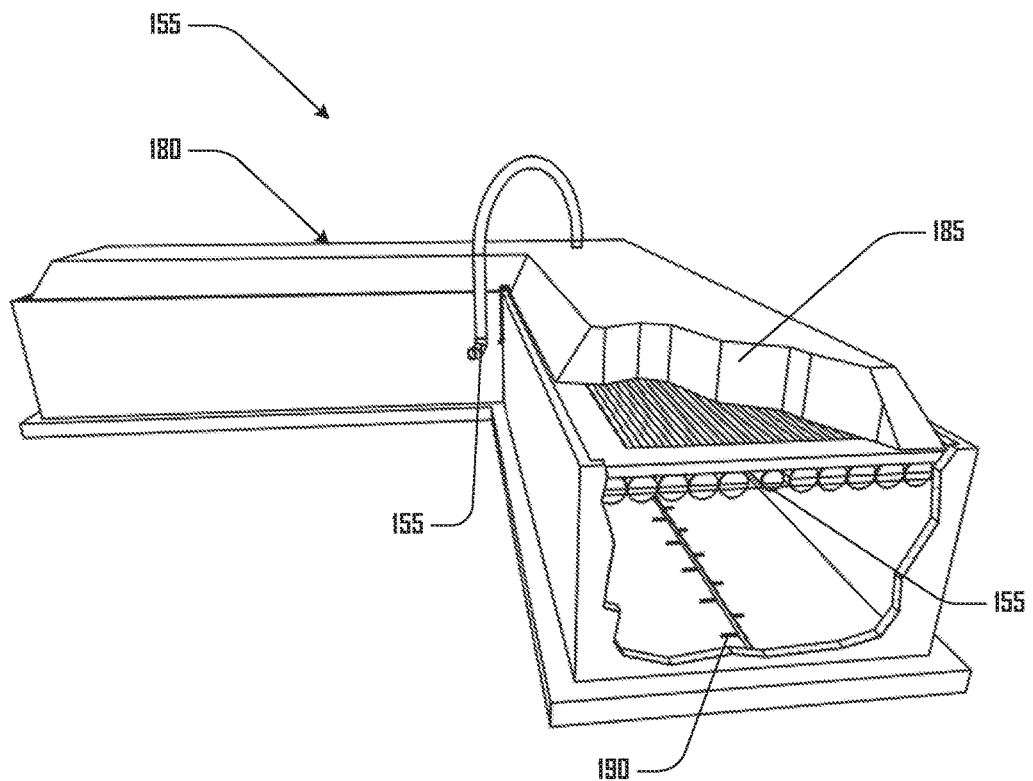
FIG. 6 illustrates an example of an embodiment of a biofilter.

A view of an example of Biofilter 155 is illustrated in FIG. 6. Biofilter 155 in FIG. 6 is illustrated as having an "L" or "bat wing configuration" above Corner Vault 166, though it may have a different shape. As illustrated in FIG. 6, Biofilter 155 may comprise a Floating Dock 180 floating on a body of water. The body of water may be in a water catchment vessel, such as Corner Vault 166. Floating Dock 180 may float on water. Legs, or the like, may support Floating Dock 180 if/when water within the catchment vessel falls below a threshold. A surface of Floating Dock 180 may comprise a structural support and a porous surface or membrane. The porous surface or membrane may support a Biofilter Media 185. Air may be introduced into the water catchment vessel via Aeration Pipes 190 and may then bubble up through the water in the water catchment vessel, thereby maintaining an aerobic condition in the water in the water catchment vessel. The air exiting the water may then pass through Biofilter Media 185 before exiting Biofilter 155. Passage of such air through Biofilter Media 185 may simultaneously reduce odors in the air and may moisturize Biofilter Media 185 with moisture from the water catchment vessel.

As noted, an air handling system may collect air above Bulk Material Wheel 105, such as from vacuums located above where bulk material is being deposited in Bulk Material Wheel 105, where bulk material is being turned over, and from air nozzles located below Bulk Material Wheel 105. Air handling system may comprise ducts, pipes, or other conduits to transport collected air; some of such conduits may be on a pivot arm. Collected air may be bubbled into one or more water catchment vessels and through Biofilter 155. Collected air may comprise dust, odors, a temperature, or the like. Dust and/or odors may be reduced and/or a temperature of process air may be altered by being bubbled through such water and through such Biofilter 155.

Figure 8:
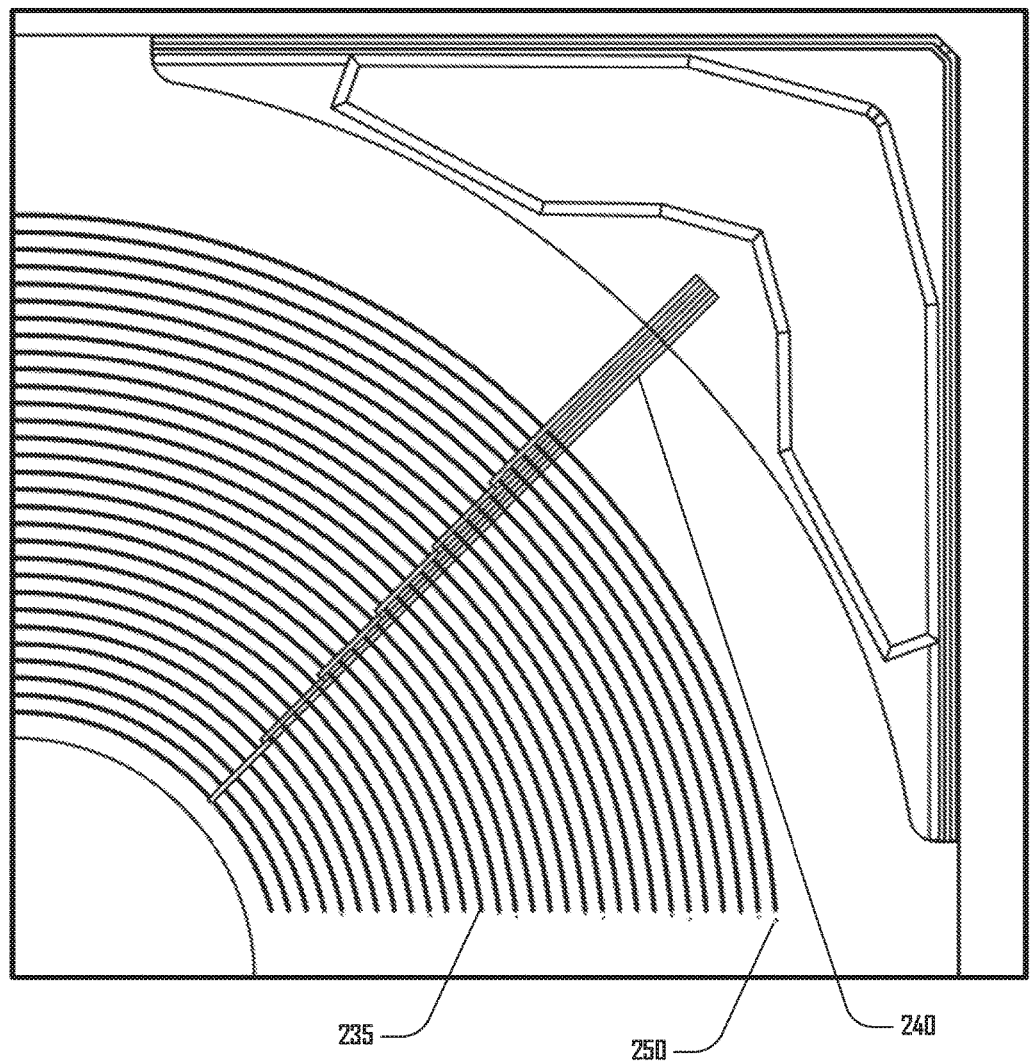
FIG. 8 illustrates an example of an embodiment of components of an air handling system.
Figure 9:
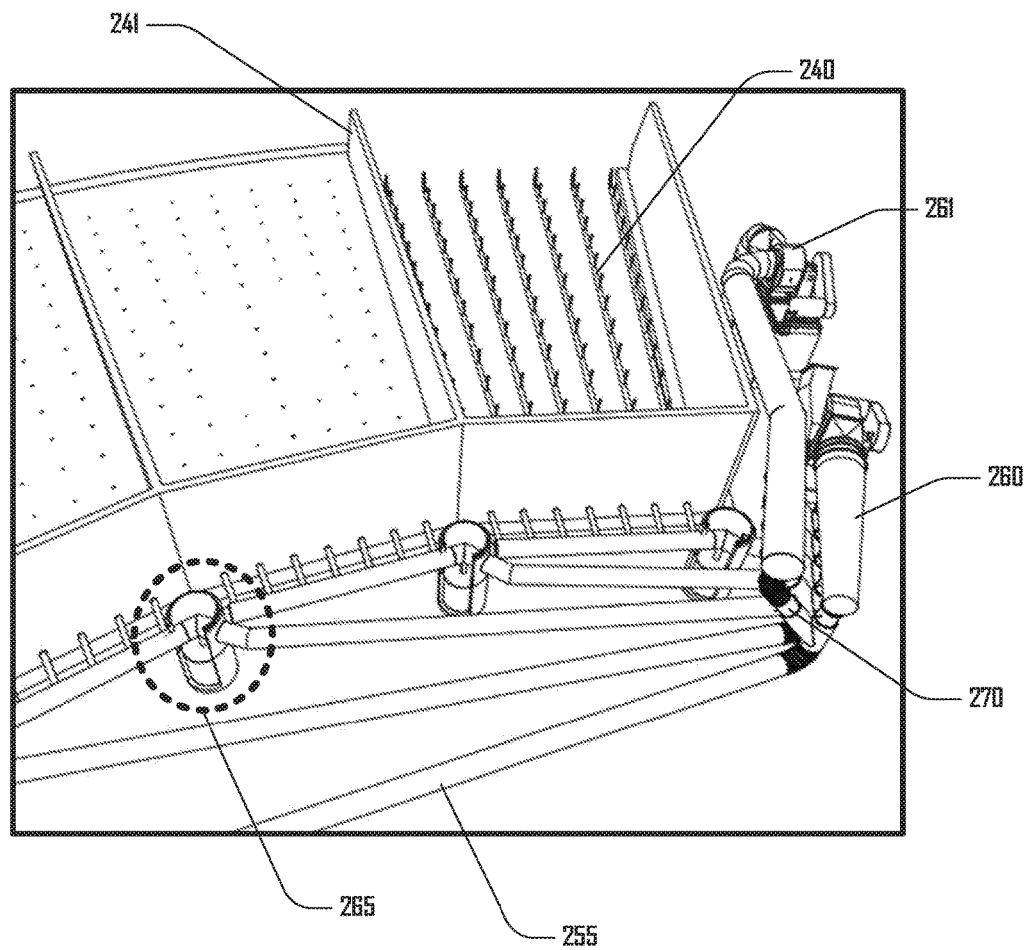
FIG. 9 illustrates an example of embodiments of first details of components of an air handling system.
Figure 10:
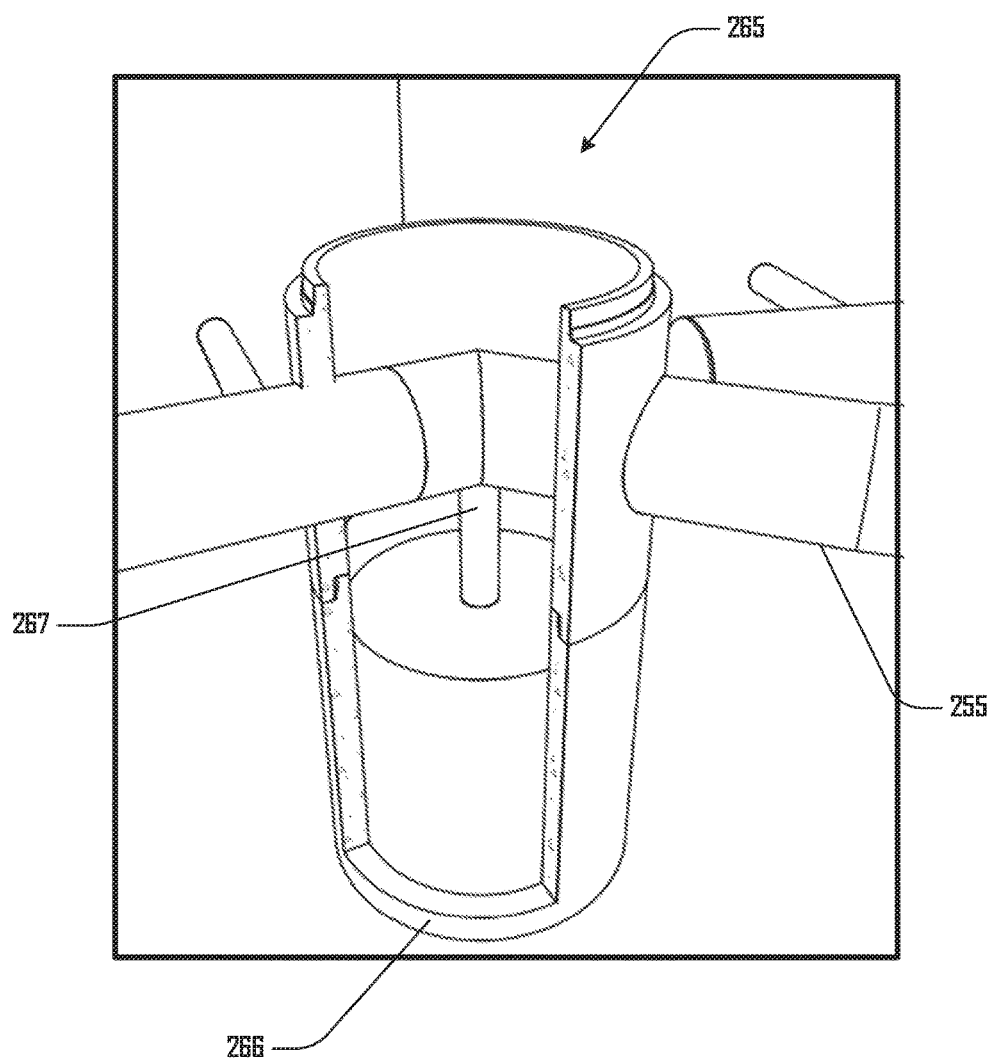
FIG. 10 illustrates an example of embodiments of second details of components of an air handling system.

FIG. 9 illustrates an example of an embodiment of Air Nozzle-Pad Assembly 195. Air Nozzle-Pad Assembly 195 may be present in, for example, Pad 106. Air Nozzle-Pad Assembly 195 may be assembled prior to pouring concrete of Pad 106. Beneath Air Nozzle-Pad Assembly 195 may be a pipe, Nozzle Feeder Pipe 230, to connect Air Nozzle-Pad Assembly 195 to negative or positive air pressure from an air handling system. Nozzle Feeder Pipe 230 may be for example, a curved lateral pipe, such as Curved Lateral Pipe 235 illustrated in FIG. 8 or a radially oriented lateral pipe, such as Radially Oriented Lateral Pipe 240 illustrated in FIG. 9.

Figure 7:
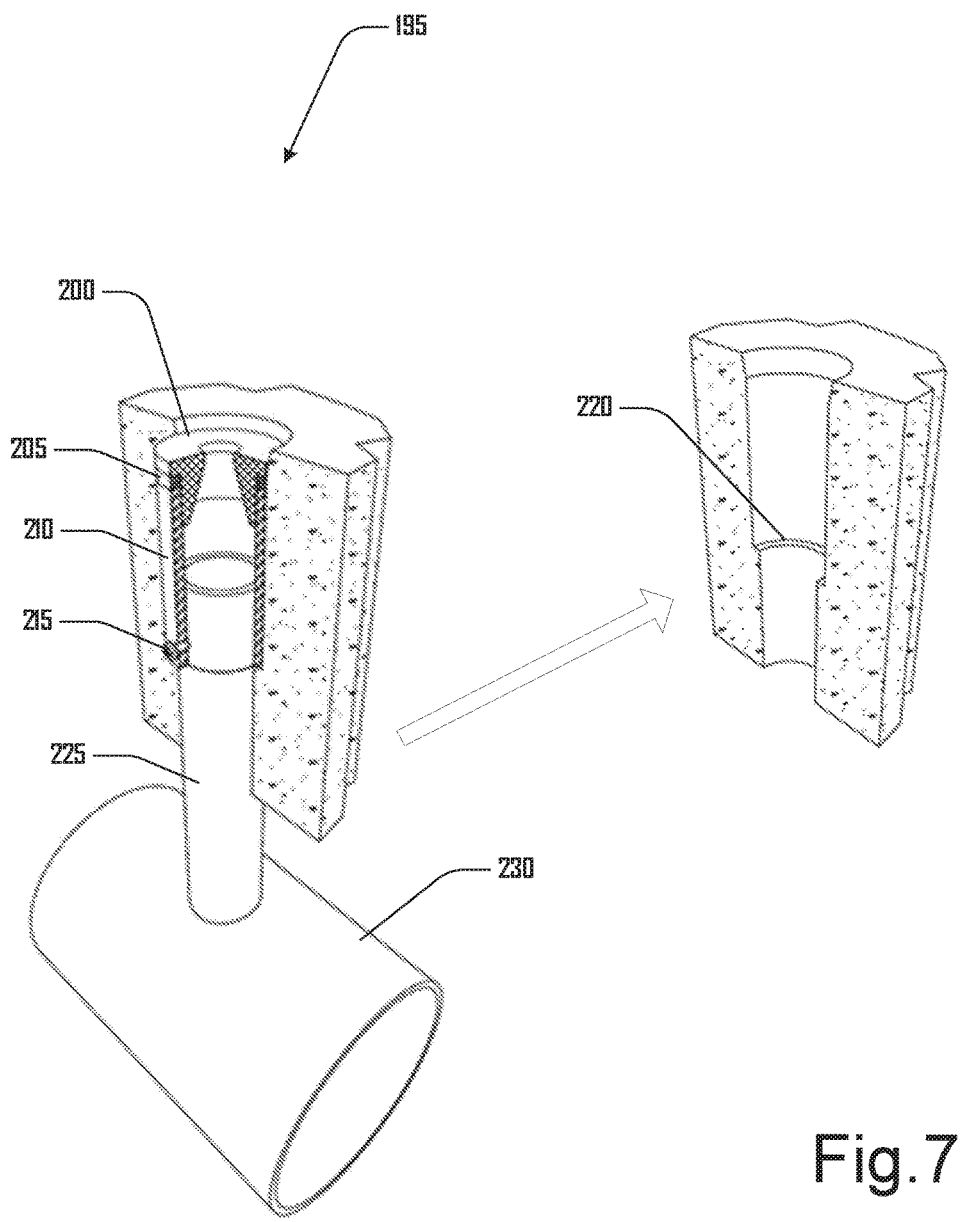
FIG. 7 illustrates an example of an embodiment of an air nozzle-pad assembly.

Air Nozzle-Pad Assembly 195 may connect to Nozzle Feeder Pipe 230 via a connection pipe, such as, for example, Spigot Pipe 225 in FIG. 7. As illustrated in FIG. 7, Spigot Pipe 225 may extend up within (or around) another pipe, such as Slider Pipe 210. During fabrication of Air Nozzle-Pad Assembly 195, Slider Pipe 210 and Spigot Pipe 225 may be secured in a desired relationship, such as by Set Screw 215. A base of Slider Pipe 210 may form Structural Shelf 220 within Pad 106, when concrete for Pad 106 is poured. Structural Shelf 220 may provide structural support for Slider Pipe 210, Spacer Ring 205, and Nozzle 200.

Atop Slider Pipe 210 may be one or more Spacer Ring 205 and, atop Spacer Ring 205, may be Nozzle 200. During assembly, one or more Spacer Ring 205 may be placed on top of Slider Pipe 210, Nozzle may be placed or secured on top of Spacer Ring 205, and a plug may be placed atop Nozzle 200. A desired elevation of a top of Nozzle 200 relative to a poured surface of Pad 206 may be achieved during fabrication by adjustment of Slider Pipe 210 and Spigot Pipe 225 through the use of Set Screw 215. After Pad 106 is poured, the plug atop Nozzle 200 may be removed and/or drilled through (to form or expose the opening in Nozzle 200). During use, and as Pad 106 wears down, Nozzle 200 may be removed from Slider Pipe 210 and one or more of Spacer Ring 205 may be removed, allowing Nozzle 200 to be recessed within Pad 106, notwithstanding that a surface of Pad 106 may wear over time. Nozzle 200 may be held in place by friction, by a threaded connection with Slider Pipe 210, by adhesives, or the like. A size of an air orifice in Nozzle 200 may be changed, such as to accommodate different anticipated air speeds. Such size may be set when Nozzles 200 is installed and may involve drilling the air orifice to the desired size and/or Nozzles 200 with different size air orifices may be installed over time.

FIG. 8 further illustrates example embodiments in which Manifold Pipes 240 connect to Curved Lateral Pipes 235 and in which Clean Outs 250 may be present, to allow Curved Lateral Pipes 235 and/or Manifold Pipes 240 to be cleaned.

FIG. 9 further illustrates example embodiments in which Radially Oriented Lateral Pipes 240 are fed by Supply Pipes 255, from Large Manifold Pipes 260, with Water Trap 265 provided to collect water and solids which may enter Nozzle 200. In the example embodiment illustrated in FIG. 9, Zones 241 may be within Pad 106. Zones 241 may have walls or barriers, as illustrated in FIG. 9 or may not. Separate aeration zones may be established in Zones 241 to allow airflow into or out of corresponding zones of Bulk Material Wheel 105 to be adjusted to meet the process temperature or moisture targets of a particular zone and/or as the bulk material is relocated among zones. One or more Blowers 261 and/or a cyclotron separator of an air handling system may be connect to Large Manifold Pipes 260, which may branch into several Supply Pipes 255 via Directional Air Flow Dampers 270, to be used to control the total air flow and direction of airflow entering each aeration zone. A Supply Pipe 255 may branch to a set of Radially Oriented Lateral Pipes 240 of a Zone 241 to distribute air to or with draw air from the process floor of Pad 106 in the zone.

Air can be positive or upward into a pile of bulk material or negative or downward, drawing air out of the bulk material pile. Airflow may alternate between the two directions to control temperatures and oxygen levels throughout the full depth of the bulk material pile. By increasing pressure within the pile, and then reducing pressure below atmospheric pressure in the pile, and alternating directional flow many times an hour, oxygen moves further into the composting particles and thin water films, as a form of forced respiration on a large pile. The greater the pressure difference the greater the penetration of oxygen into the water films and composting particles.

To keep Nozzles 200 clean during turning and reloading operations, a flushing system may clean Nozzles 200. The flushing system may comprise cleanouts and/or high velocity upward airflow or water flow provided to Nozzles 200. Some bulk material and/or water may fall through the nozzles during processing; cleanouts, such as Cleanout 250, and/or Water Trap 265, may be provided to allow such bulk material and/or water to be cleaned out. Such cleanouts may be provided, for example, at the ends of Radially Oriented Lateral Pipe 240, along Supply Pipes 255, or along Curved Lateral Pipe 235. Cleanouts may comprise a cap or lid to allow access and/or cleanouts may comprise piping to allow automated clean-out.

In an embodiment of a cleanout illustrated by way of example in FIG. 9, Water Trap 265 may comprise a Water Trap Tank 266 and Vertical Pressure Trap Pipe 267. Water Trap Tank 266 may drain to a water catchment vessel, either through gravity or a pump or may be accessed via a cap on Water Trap Tank 266. Vertical Pressure Trap Pipe 267 may provide air or water under pressure to force out water and/or solids which may accumulate in Water Trap Tank 266.

A temperature of air in an air handling system may be sensed modified, such as to increase or decrease the temperature. Modification of the temperature may be through a heating or cooling system which actively or passively transports heat energy between a volume of air in the air handling system and a heat sink or heat source. The heat sink or heat source may be one of Pad 106, ground beneath or proximate to Pad 106, a volume of water, or a volume of air.

The surrounding soils may be used as a heat sink or heat source to stabilize process air temperatures. During hotter weather, bulk material may be aerated predominantly in a positive mode to cool air in the bulk material below ambient temperatures. During cooler weather, bulk material piles may be aerated predominantly in a negative mode to conserve and/or return heat below ground. Regulating the temperature of the process air may reduce the need for cooling process air entering a biofilter odor control system, such as Biofilter 155. The biofilter odor control system may require normal operating conditions of 55 to 104 degrees Fahrenheit.

Figure 11:
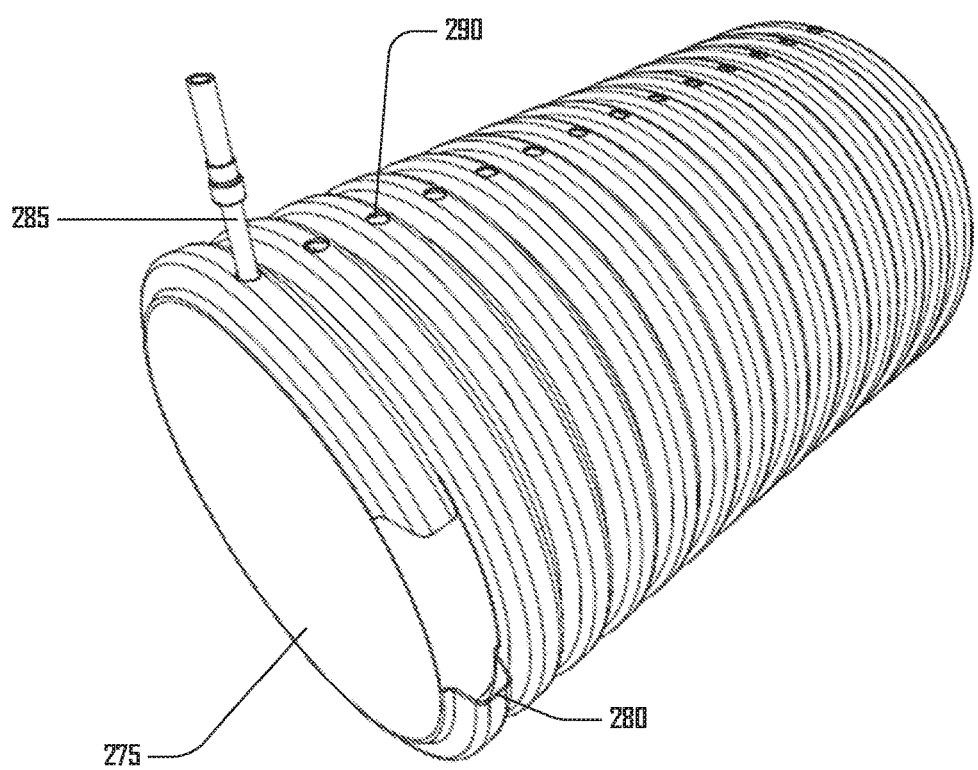
FIG. 11 illustrates an example of embodiments of third details of components of an air handling system.

To increase thermal contact between air ducts, manifolds, or the like and Pad 106 and/or ground beneath or proximate to Pad 106 and to increase the heat holding capacity, such air ducts may comprise channels that may be filled with water. For example, FIG. 11 illustrates an air pipe, duct, or the like, Duct 275, which may transport air of the air handling system. Duct 275 may be an inexpensive and standard material, such as reinforced, corrugate plastic or polyethylene pipe. Duct 275 may comprise one or more Channels 280 or corrugations surrounding a smooth central bore. Channels 280 may be filled with water, such as via Water Fill Pipe 285 and Holes 290 (which may be drilled when the unit is deployed). When air passes through Duct 275, it may exchange energy with water in Channels 280, which may exchange energy with surround media, passively raising or lowering the temperature of such air. In an embodiment, a heat exchanger may be used, for example, to raise or lower the temperature of process air or water of a water collection system.

In another embodiment, the heat sink or heat source may be water of a water collection system, such as water in a water catchment vessel. Air ducts may pass through a water catchment vessel and/or air in the air ducts may be bubble through a water catchment vessel and/or air filter, as discussed herein. Water from the water collection system may be sprayed into a volume of air to transfer heat energy between the water and the air.

The air handling system may inject air into or withdraw air from Bulk Material Wheel 105, such as via Nozzles 200. The air handling system may also collect air from locations around Pad Layout 100. For example, the air handling system may collect air from ducts proximate to where bulk material is deposited on Bulk Material Wheel 105, areas where bulk material in Bulk Material Wheel 105 is being turned over, and/or from an air knife/vacuum which may be used to remove plastics and the like from bulk material.

Figure 12:
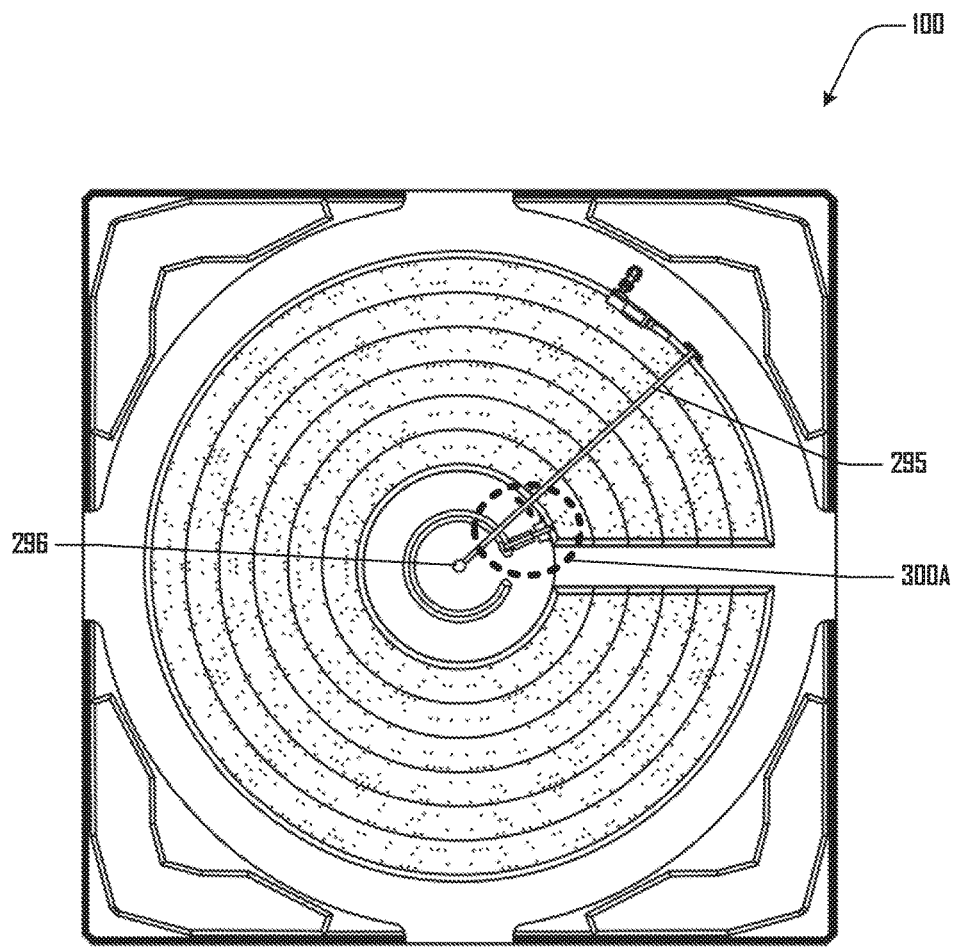
FIG. 12 illustrates an example of embodiments of a compost system site and compost handling equipment.

As illustrated in FIG. 12, an embodiment of Site 100 may comprise Pivot Arm 295. Pivot Arm 295 may comprise Pivot 296, about which Pivot Arm 295 may rotate. Pivot 296 may be anchored in Site 100, such as in a center of Site 100. Rotation of Pivot Arm 295 around Pivot 296 may be as a result of a motor and ground carriage on or of Pivot Arm 295 and/or rotation of Pivot Arm 295 may be as a result of movement of mobile equipment tethered to Pivot Arm 295, such as compost handling equipment. Rotation of Pivot Arm 295 may be automated.

Pivot Arm 295 may further comprise sensors to detect, for example, a position of Pivot Arm 295, a location and orientation of compost handling equipment, a depth of bulk material, a moisture content of bulk material, an air quality, a humidity and/or rainfall, a barometric pressure, an electrical or magnetic field, or the like. Position and location sensors may utilize, for example, multi-lateration using Global Positioning System (GPS), WiFi, or other wireless signals, inertial measurement units, compasses, relative position or "index" sensors (such as Hall Sensors), and the like. Depth of bulk material may be measured using millimeter wave electromagnetic radiation or the like.

Figure 13:
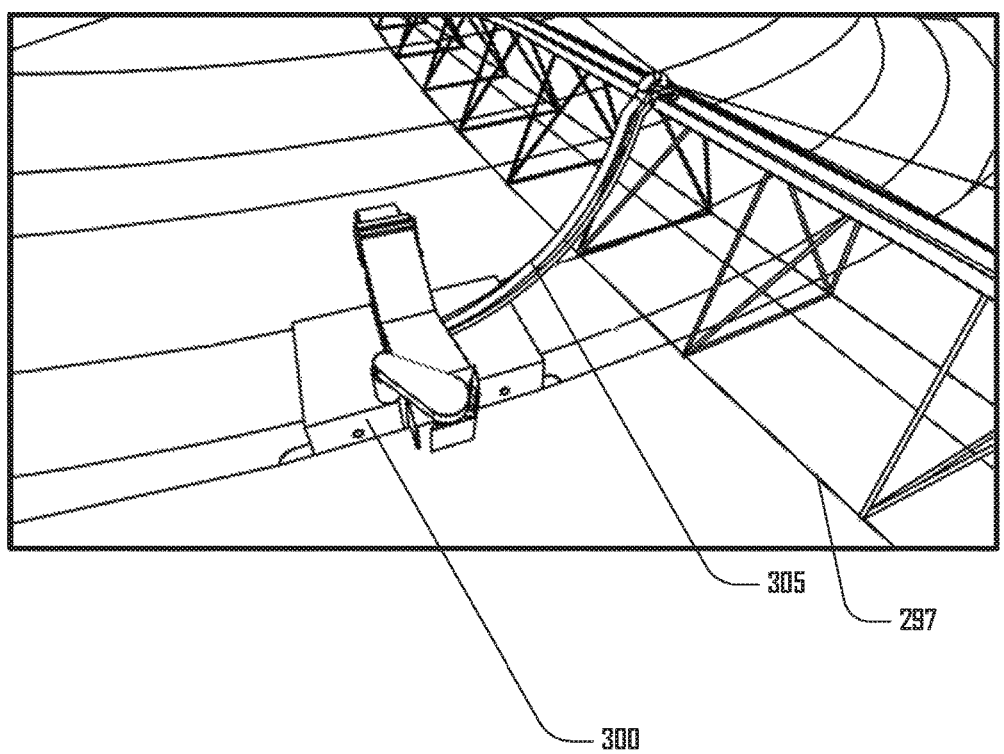
FIG. 13 illustrates an example of embodiments of first details of a pivot arm and compost handling equipment.

Compost handling equipment, whether attached to a pivot arm or freely operating in Site 100, may comprise, for example, a mobile compost turner and screener 300A, a grinder, a screener, and/or a loader. Some of such compost handling equipment may be mobile. Some compost handling equipment may be attached to a pivot arm by a tether. For example, FIG. 13 illustrates Tether 305 attached to Pivot Arm 297 and Mobile Equipment 300. Tether 305 may allow Mobile Equipment 300 a range of independent motion, relative to Pivot Arm 297. Tether 305 may provide electrical power, data connection, fossil fuel, water, oil, hydraulic fluid, and the like to an attached mobile equipment.

Figure 14:
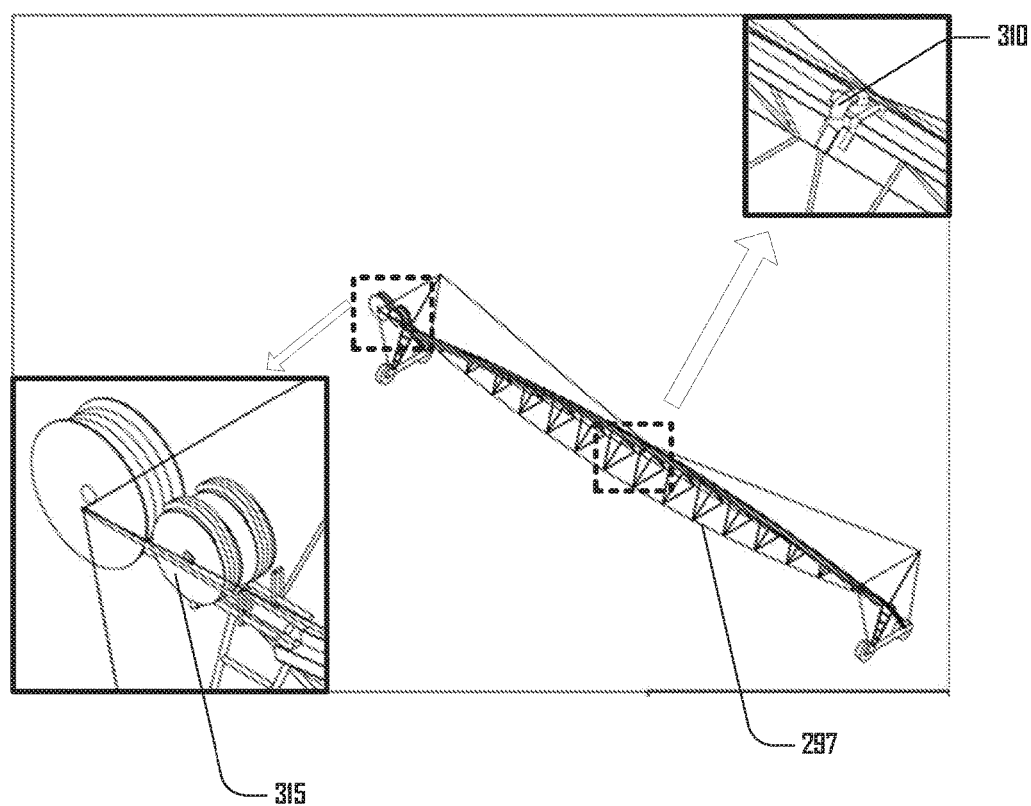
FIG. 14 illustrates an example of embodiments of second details of a pivot arm.

A tether may be attached to a pivot arm by a carriage. For example, FIG. 14 illustrates Tether Carriage 310 on Pivot Arm 297. Tether Carriage 310 may allow Tether 305 to relocate along Pivot Arm 297. FIG. 14 also illustrates Reel 315. Reel 315 may be a coil of hose for air or water (whether positive or negative pressure), of electrical or data conduit, or the like. Reel 315 may service Tether 305, gathering up and releasing conduit or the like as Tether 305 moves along Pivot Arm 297. Reel 315 may serve a sprayer (or sprinkler), which may spray water onto bulk material from Pivot Arm 297. Reel 315 may serve an air handling system. The air handling system may comprise a vacuum or air pump on or proximate to Pivot Arm 297 or on or proximate to mobile equipment; such vacuum or air pump may connect to Pivot Arm 297 and Reel 315.

Figure 15:
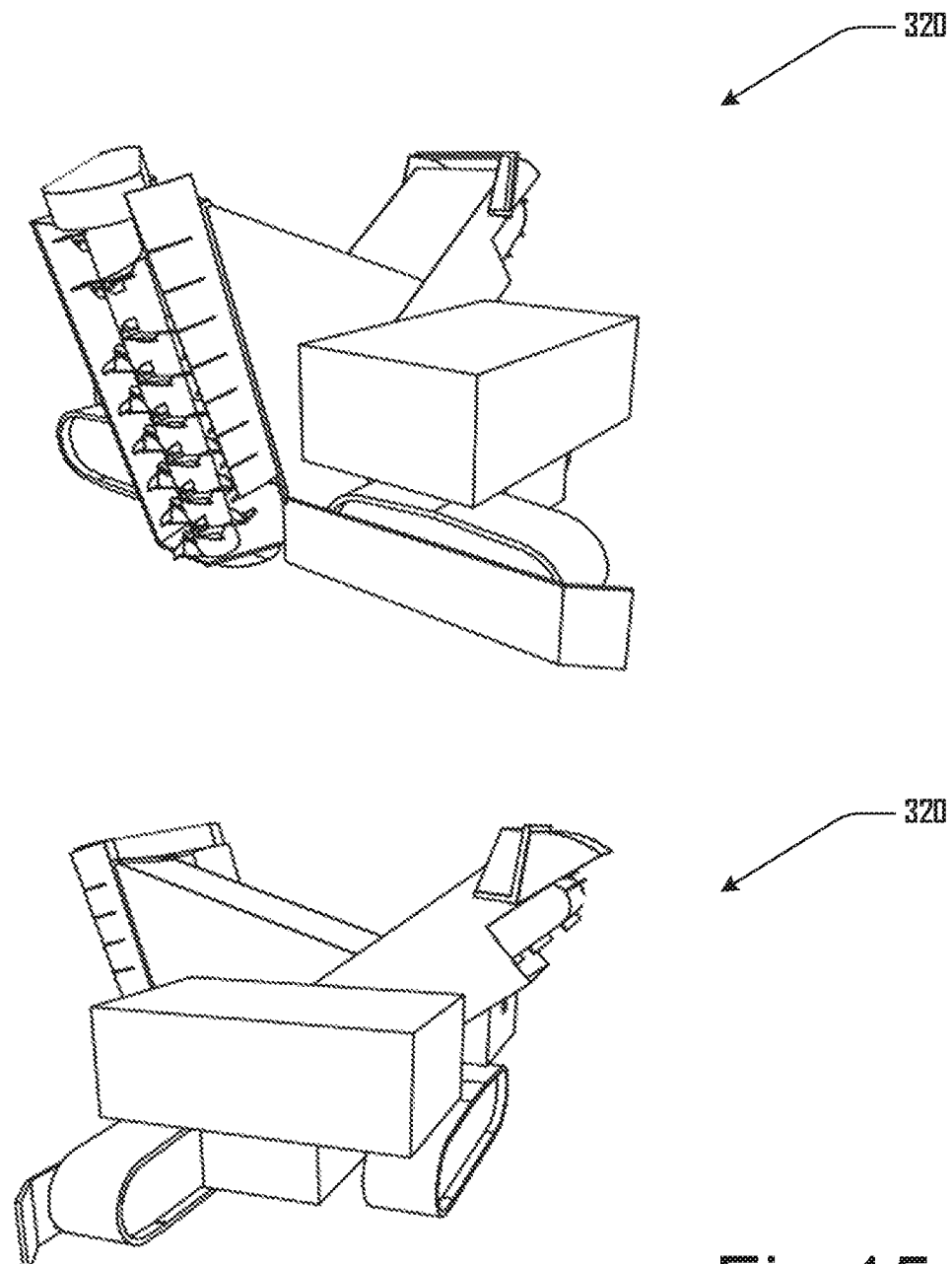
FIG. 15 illustrates an example of embodiments of a compost turner.

FIG. 15 illustrates an example of mobile compost equipment which may be tethered to a pivot arm; in the embodiment illustrated in FIG. 15, the mobile compost equipment may be Turner 320. Turner 320 may be used to agitate and move material radially toward the center of a circular pad. Turner 320 may rest on the sloping side of a large windrow or pile (which naturally forms a trapezoidal shape). A capacity of Turner 320 may be, for example, about 2,000 cubic yards/hour for a self-propelled unit with 180 kW of available power. Turners operated by people may have to be larger to accommodate humans who do not work 24 hours/day, 7 days/week. Turner 320 may be characterized by having one or two rotors, with inclined or horizontal axis; the rotors may remove vertical layers of the material from the existing windrow and convey them laterally to form a new windrow. As the turner moves along the side of the windrow, rotating plates or teeth or the like may shave off a layer of compost and deposit it on a conveyor. The conveyor moving the compost determines the location and height of the new windrow. The plates or teeth on Turner 320 may be changed to provide more or less shredding action. Turner 320 may be self-propelled or pulled by tractor, PTO driven or self-powered. The system described herein may avoid the requirement of traveling lanes that require greater land area.

Turner 320 may be mobile with a ground drive system and may be tethered to the pivot arm for guidance, as illustrated in FIG. 13 (in the case of Mobile Equipment 300 being Turner 320). Tether 305 of FIG. 13 may provide direction and speed control to the ground drive system on Turner 320. The radius of a working face that Turner 320 may agitate along Bulk Material Wheel 105 may be controlled or facilitated by indexing the Turner 320 and Tether 305 inward or outward on Pivot Arm 297 using, for example, Tether Carriage 310.

Turner 320 may have the ability to cut into the bed of bulk material and place the bulk material onto a conveyor system to relocate the bulk material toward the center of circular pad and continually open up a lane for the turner to move toward the outside of Bulk Material Wheel 105. Once Turner 320 reaches the outside of Bulk Material Wheel 105 or once Turner 320 reaches a keyway, such as Keyway 110 of FIG. 1, Turner 320 may be guided back toward the center of Pivot Arm 297 along the keyway. In order to maintain a clear lane and avoid obstruction of Turner 320, Turner 320 may have a scraper or sweeper attached to a side of Turner 320 to move bulk material aside.

Turner 320 and/or a pivot arm may have the ability to spray water onto the bulk material as it is being conveyed toward the center of the pile. Water sprayed onto bulk material may be from a water catchment vessel. Such water may be pumped along pivot arm, and out onto the bulk material and/or out through a tether to mobile equipment. Turner 320 may also have dust, plastic, and odor collection system; such a system may vacuum air from a location where Turner 320 cuts into and discharges the bulk material.

Automatic operation of Turner 320 may reduce the need for a higher production trapezoidal turner and may reduce or eliminate the need for an operator. In legacy systems, a pad size holding 42,000 cubic yards of bulk material would require 35 hours of normal trapezoidal turner operation at 1,200 cubic yards an hour and would require an equipment operator to direct the turner, which may limit hours of operation. Thus the 35 hours of normal operation time may be spread out over approximately one working week. Utilizing the system disclosed herein, the same work can be accomplished by a smaller automated turner, one capable of 350 cubic yards per hour or only 40 kW of available power based on a 5 day turning cycle.

Figure 16:
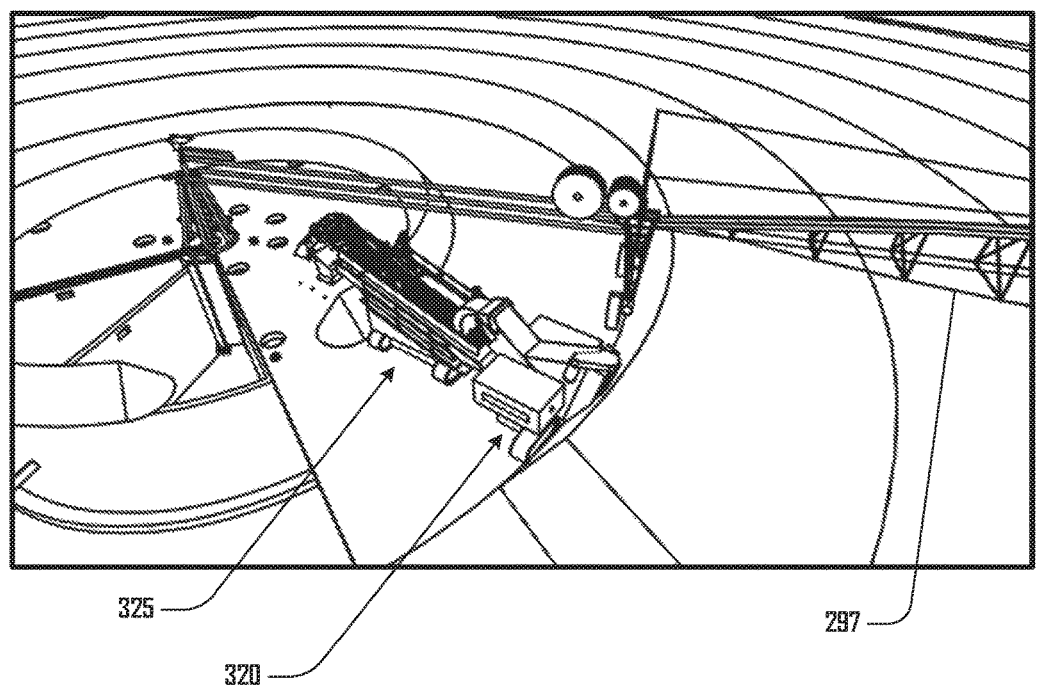
FIG. 16 illustrates an example of embodiments of a pivot arm and compost handling equipment.

FIG. 16 illustrates an example of mobile equipment comprising Turner 320 and Screener 325 to create a uniform salable product. Turner 320 can automatically load material from Bulk Material Wheel 105 directly onto Screener 325 without requiring the use of a front end loader or other material handling equipment. Screener 325 is illustrated in FIG. 16 as being tethered to Pivot Arm 297 to allow for delivery of power and collection of dust and odors during screening. Screener 325 may have its own automated ground drive system and sensors to determine the appropriate loading rate from Turner 320 to Screener 325. In addition and/or alternately, Pivot Arm 297 may have a conveyor to move bulk material from Turner 320 and/or Screener 325, to relocate the bulk material from the center to the perimeter of the circle for screening and removal.

Figure 17:
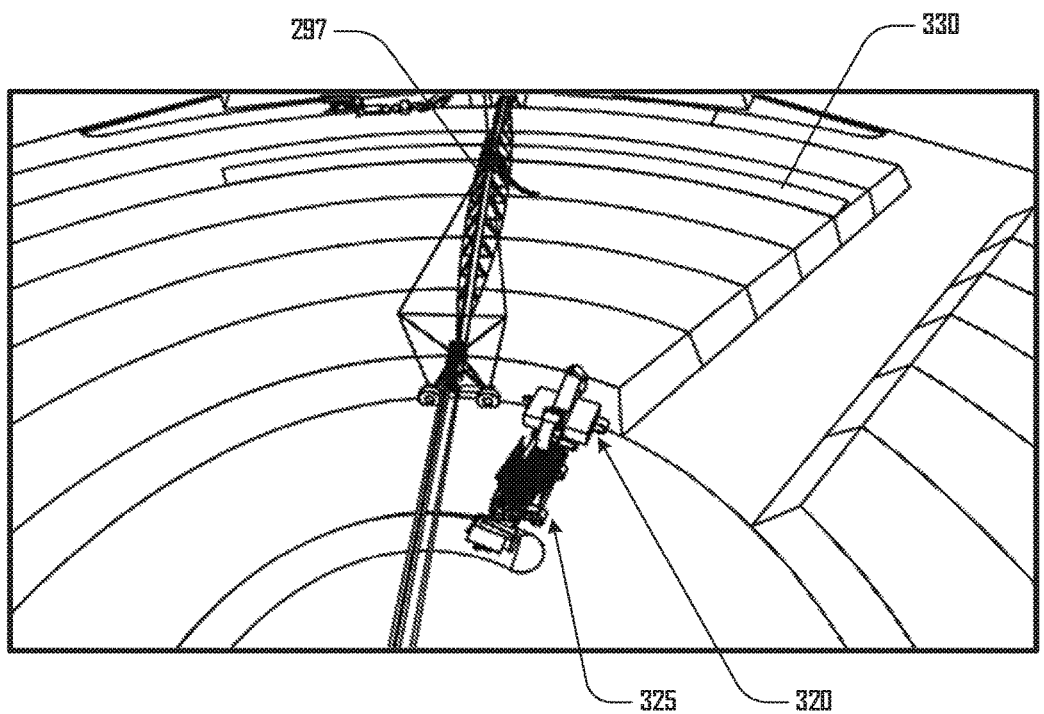
FIG. 17 illustrates the example of embodiments of the pivot arm and compost handling equipment of FIG. 16, from a different view.

FIG. 17 provides another view of an embodiment of Turner 320, Screener 325, and Pivot Arm 297. In this embodiment, Turner 320 obtains bulk material from the inner aeration zone and turns over and/or deposits bulk material on Screener 325. Screener 325 may place the finished screened fine compost into a single circular windrow near center pivot and/or into a loader or truck for delivery to market. Larger materials from Screener 325 may be conveyed by a conveyor on or of Pivot Arm 297 (example embodiments of such a pivot arm are illustrated herein) to the outer aeration zones to form an odor controlling Biocover 330 and to allow further composting time for the woodier fractions in the overs. Reuse of screened overs after turning the biocover back into the composting media also assures that the composting media is porous enough to allow good airflow through the pile, and to help buffer an initial pH drop in incoming feedstocks.

Figure 18:
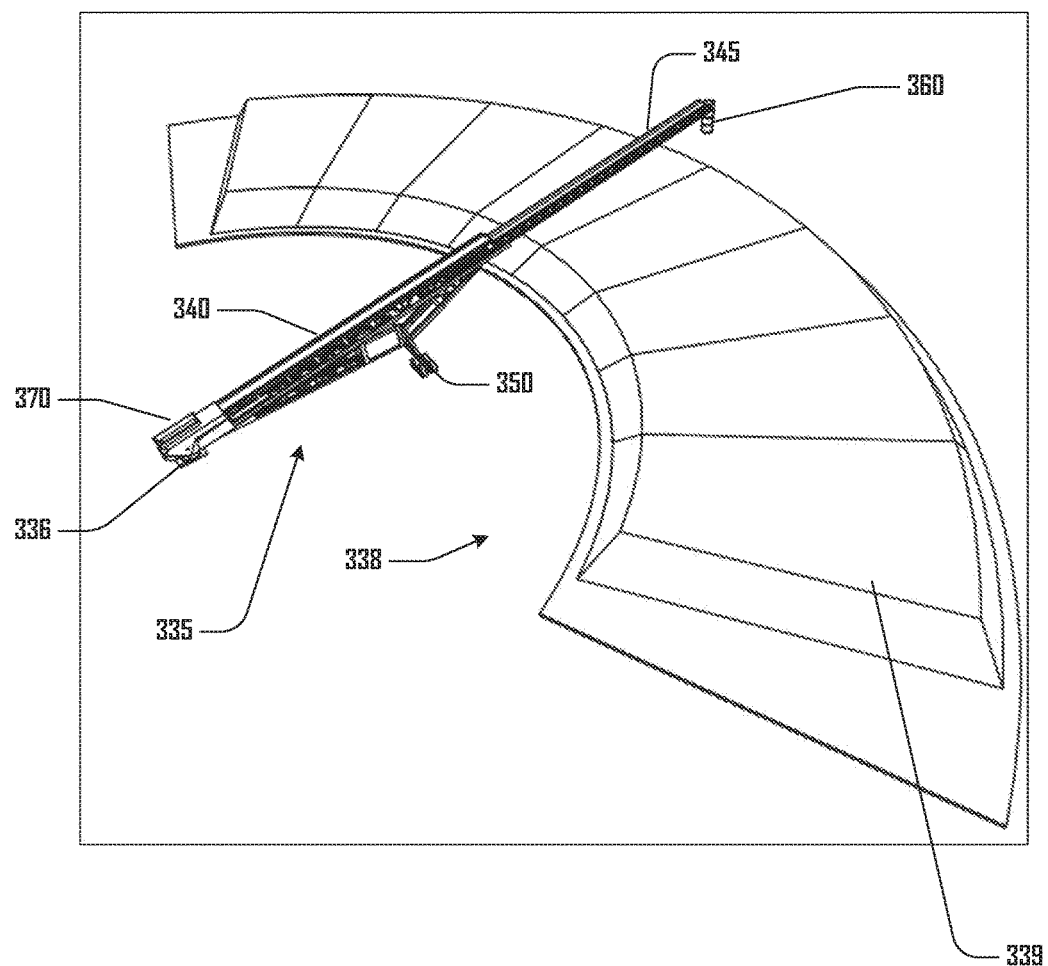
FIG. 18 illustrates an example of embodiments of a pivot arm and a first bulk material arrangement.

FIG. 18 illustrates embodiments of a Pivot Arm 335 and of a portion of a Segmented Bulk Material Wheel 340. In these embodiments, Pivot Arm 335 comprises a Ground Drive System 350, a Primary Conveyor 340, an Outer Conveyor 345, and a Drop Tube 360. Ground Drive System 350 may be used to rotate Pivot Arm 335 around Pivot 336. Outer Conveyor 345 may be drawn into or extended from Primary Conveyor 340, in a telescoping manner. In a telescoping conveyor, one or more overlapping conveyors are stacked beneath one another. Outer conveyor(s) slide out from beneath a primary conveyor. Material on the conveyors drops from one conveyor to the next as the material progresses toward an end of the conveyors.

Bulk material may be deposited on Primary Conveyor 340 by a hopper at or above Pivot 336, such as Hopper 370. Hopper 370 may be positioned at or above Pivot 336 so that bulk material or other material may be deposited in Hopper 370 as Pivot Arm 335 rotates. A grinder, shredder, and/or screener may operate in conjunction with Hopper 370, to grind, shred, mix, and/or screen bulk material before being loaded into the conveyor.

Bulk material deposited on Primary Conveyor 340 may be carried by Primary Conveyor 340 and Outer Conveyor 345 for deposition on an aeration pad, such as Pad 106 illustrated in FIG. 1. Through the action of the conveyors, Ground Drive System 350, and Rotating Flail 355 (illustrated in FIGS. 21 and 22), bulk material may be automatically deposited by Pivot Arm 335 to form a Bulk Material Wheel 338. The bulk material may be deposited in pie-shaped segments or zones, such as Bulk Material Segment 339. Each segment or zone may be a discrete batch of composting material in a particular stage of processing. Each zone can be separated physically by a partition wall, such as Partition Wall 365, illustrated in FIG. 20, or by differentiating the character of the material, as may be achieved by depositing bulk material at different times, to produce distinctions of color or consistency.

Partition Walls 365 may define a bunker with two sides and an end wall; an open end of the bunker may allow access to, for example, unload the bunker after it has degraded, to load the bunker (for example, in a case in which loading the bunker may be done by a loader), or to service components of the bunker or nozzles in the pad below the bunker. The open end of the bunker may face in toward the center of the site, or out, away from the center.

Drop Tube 360 may facilitate deposition of bulk material in a localized area. Drop Tube 360 may rotate, such as to rotate Drop Tube 360 up, such that is does not intersect (or intersects less) with the bulk material exiting Outer Conveyor 345. Drop Tube 360 may comprise water outlet(s) to apply water to bulk material inside of Drop Tube 360. For example, such water outlets may be circumferential to the inside of Drop Tube 360, pointing inward to a center of Drop Tube 360.

A conveyor of a pivot arm may be reversible and/or a second conveyor with a return path to the center of Site 100 may be located within Site 100 and/or proximate to a first conveyor. The conveyor with return path to the center of Site 100 may be used to convey bulk material from a turner or the like back to a central area, such as to be further mixed, ground, watered, screened, or processed for being brought to market.

Figure 19:
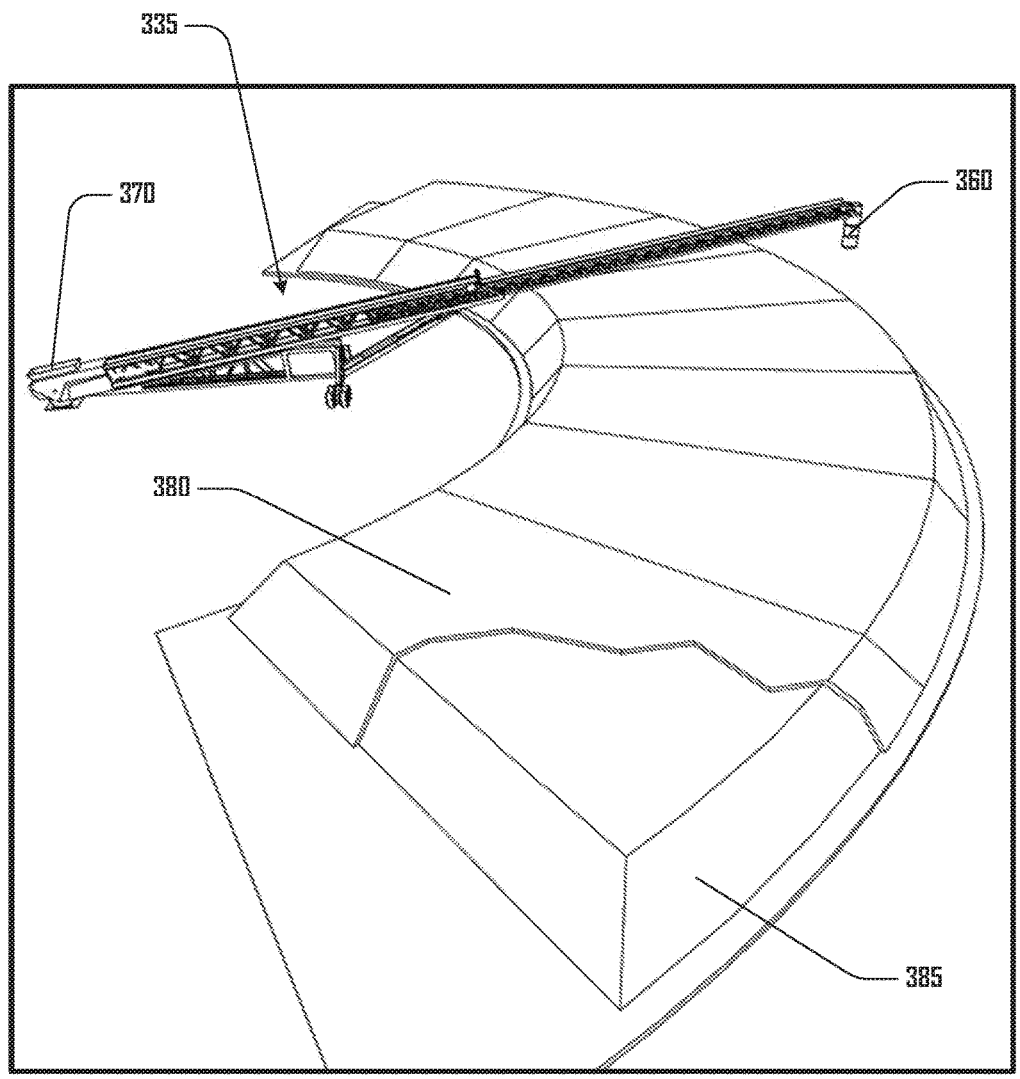
FIG. 19 illustrates an example of embodiments of a pivot arm and a second bulk material arrangement.

FIG. 19 illustrates an embodiment in which a biocover, such as Biocover 380, has been deposited on Bulk Material 385. As noted, Biocover 380 may comprise one or more material placed on the surface of bulk material for a purpose, such as to consume methane, reduce odors, reduce evaporation, provide protection from sunlight, or the like. Biocover 380 may be placed through use of Pivot Arm 335.

Figure 20:
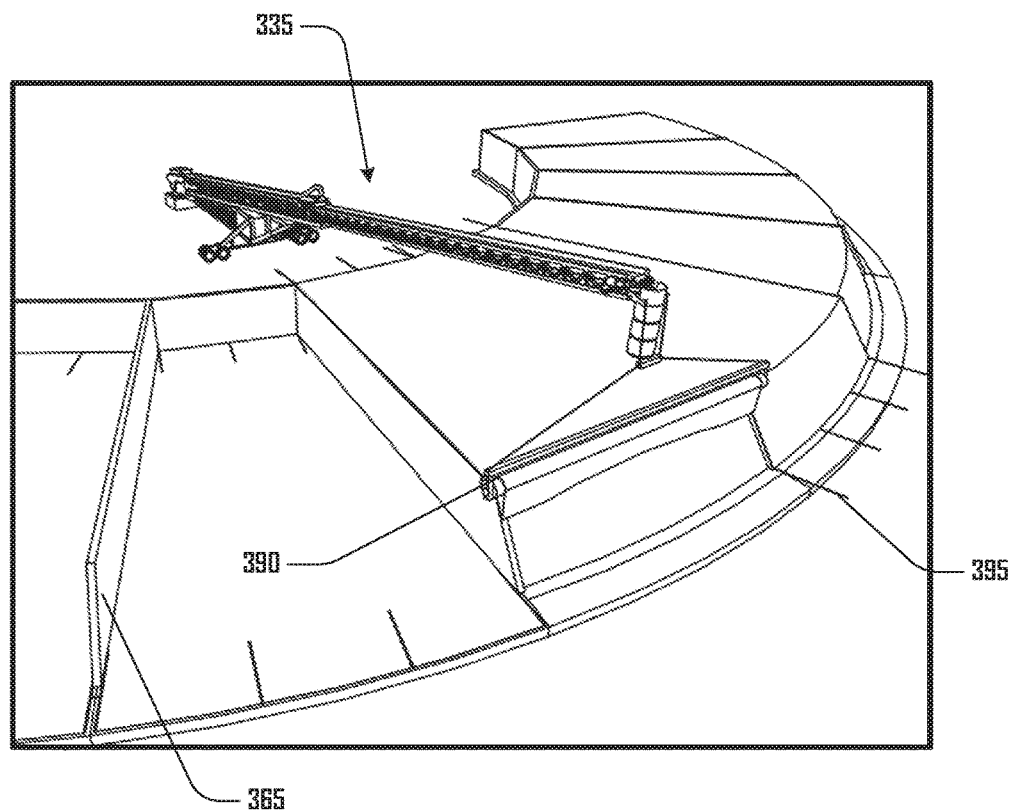
FIG. 20 illustrates an example of embodiments of a pivot arm, a third bulk material arrangement, partition walls of a bulk material pad, and a tarp roller carriage in a first position.

In an embodiment illustrated in FIG. 20, an embodiment of a tarp roller carriage, such as Tarp Roller Carriage 390, may be used to deposit a tarp, semipermeable or impermeable fabric or the like as a biocover and/or to prevent rain, sun, and other weather from affecting operations. Tarp Roller Carriage 390 may comprise a mechanical roller drum; Pivot Arm 335 may be used to deploy Tarp Roller Carriage 390 and to deploy and roll up tarp. Straps 395 may be used to secure such biocover to partitions, such as partitions defined by Partition Wall 365.

Figure 21:
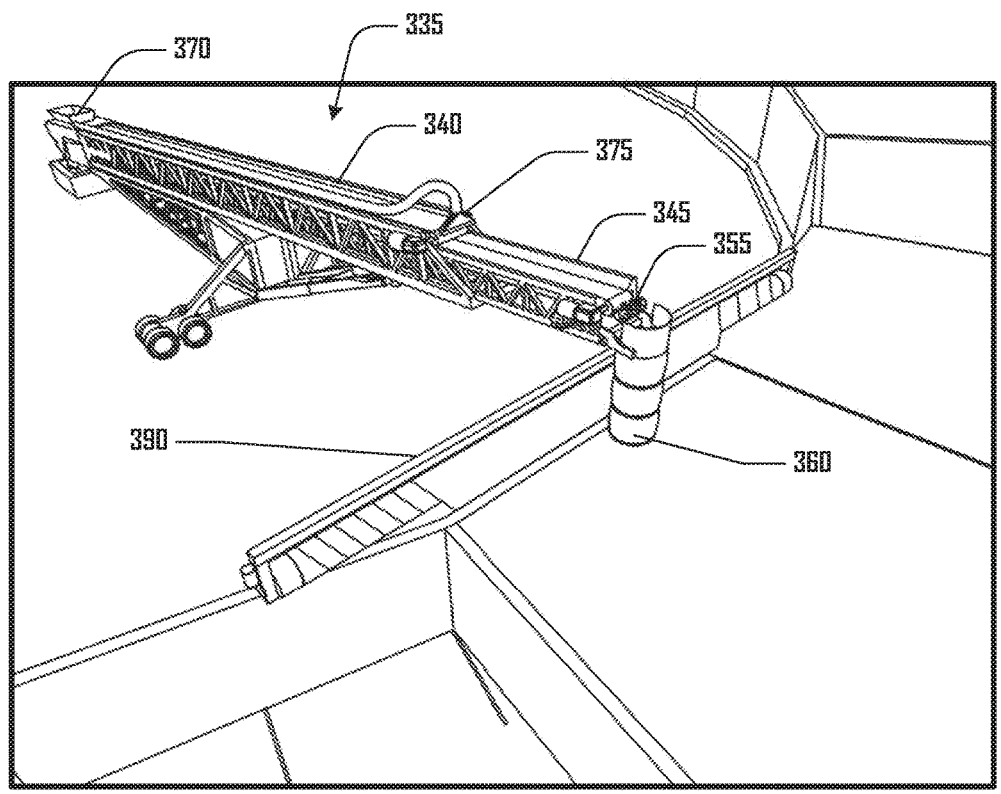
FIG. 21 illustrates an example of embodiments of the pivot arm, third bulk material arrangement, partition walls, and tarp roller carriage of FIG. 20, with the tarp roller carriage in a second position.
Figure 22:
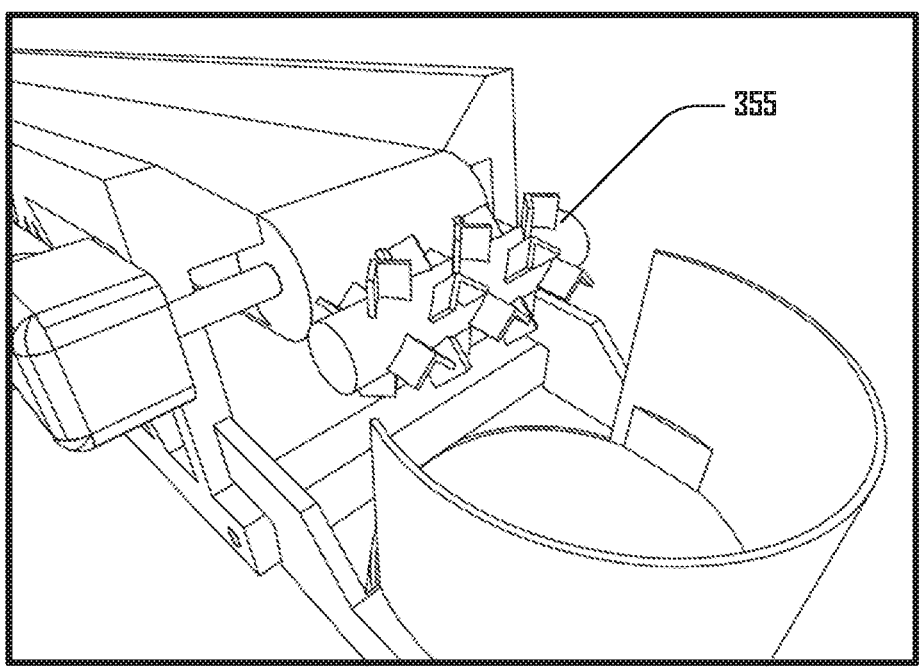
FIG. 22 illustrates an example of embodiments of a rotating flail.

In FIG. 20, Tarp Roller Carriage 390 is illustrated in an extended position. In FIG. 21, Tarp Roller Carriage 390 is illustrated in a retracted position. In addition to a closer view of components discussed in relation to other of the Figures, FIGS. 21 and 22 provide views of an embodiment of a rotating flail, such as Rotating Flail 355. Rotating Flail 355 may rotate in a first direction, which may be characterized as "outward", to facilitate movement of bulk material out from Outer Conveyor 345 onto a deposited area of bulk material. Rotating Flail 355 may rotate in a second direction, which may be characterized as "inward", to facilitate movement of bulk material downward, such as downward onto deposited bulk material Rotating Flail 355 may comprise or be proximate to water outlets, to apply water to bulk material.

Figure 23:
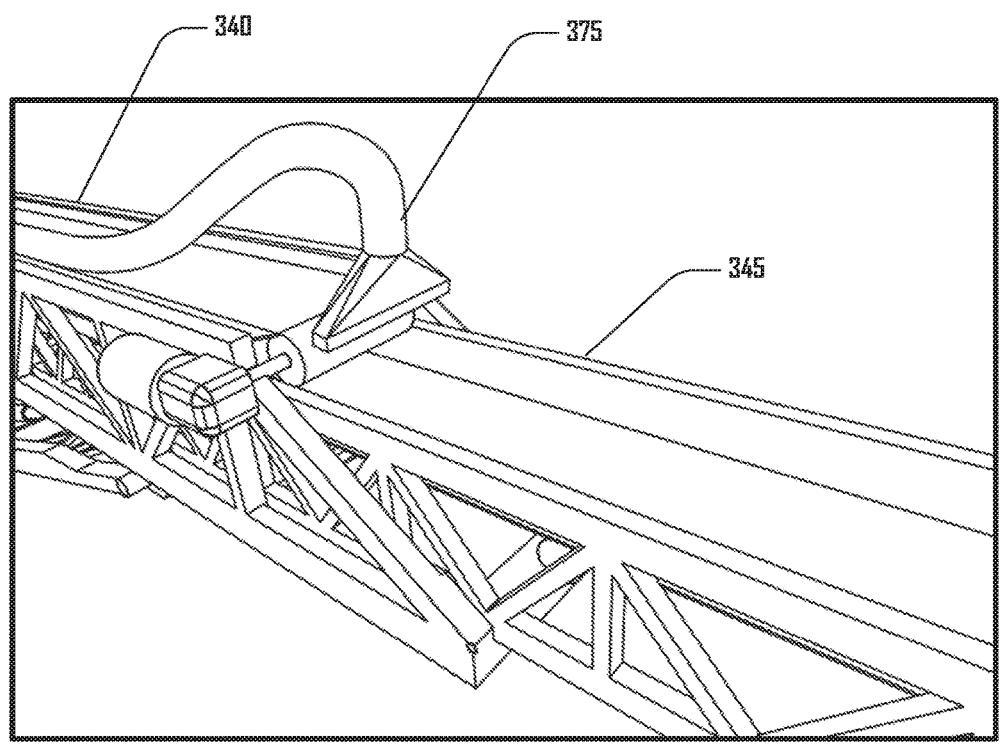
FIG. 23 illustrates an example of embodiments of an air knife vacuum head.

FIG. 23 provides a close view of an air knife vacuum head, such as Air Knife Vacuum Head 375. Air Knife Vacuum Head 375 may collect air proximate to where bulk material drops from Primary Conveyor 340 to Outer Conveyor 345. In an embodiment, a source of pressurized air, also referred to herein as an "air knife", may be directed to bulk material, such as from below or from an angle. Plastic, dust, and lower-density material in bulk material may be airborne proximate to Air Knife Vacuum Head 375 and may be collected by suction from Air Knife Vacuum Head 375. In another embodiment, a magnet may be present at such a location, to remove contaminants attracted to a magnetic field.

Figure 24:
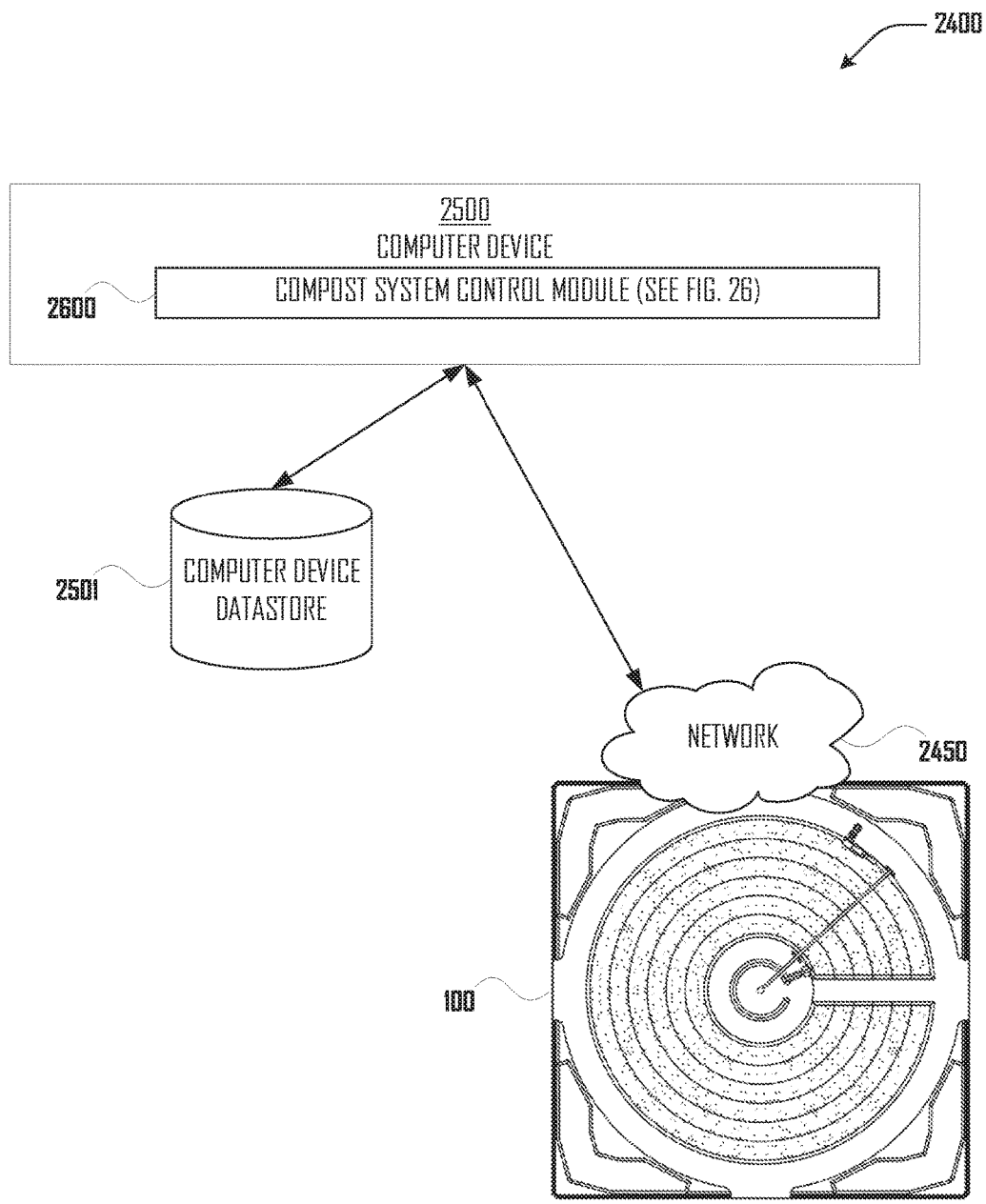
FIG. 24 is a network and device diagram of an embodiment of a computer device comprising a compost system control module in the context of a compost system site.

FIG. 24 is a network and device diagram 2400 illustrating an example of at least one computer device 2500, computer device datastore 2501, network 2450, and Site 100, which may be or comprise a compost system incorporated with the teachings of the present disclosure, according to some embodiments. In embodiments, computer device 2500 may include a compost system control module (to be described more fully below).

Computer device 2500, except for the teachings of the present disclosure, may include, but is not limited to, a server, a workstation computer, a desktop computer, a laptop computer, a tablet computer (e.g., IPAD®, GALAXYTAB® and the like), an ultraportable computer, an ultramobile computer, a netbook computer and/or a subnotebook computer; a mobile telephone including, but not limited to a smart phone, (e.g., IPHONE®, ANDROID®-based phone, etc.). Also illustrated in FIG. 24 is computer device datastore 2501. Computer device datastore 2501 is a datastore used by computer device 2500. Computer device 2500 represents one or more computers.

Also illustrated in FIG. 24 is network 2450. Network 2450 may comprise computers, switches, routers, gateways, network connections among the computers, and software routines to enable communication between the computers over the network connections. Examples of Network 2450 comprise wired networks, such as an Ethernet networks, and/or a wireless networks, such as a WiFi, GSM, TDMA, CDMA, EDGE, HSPA, LTE or other network provided by a wireless service provider; local and/or wide area; private and/or public, such as the Internet. More than one network may be involved in a communication session between the illustrated devices. Connection to Network 2450 may require that the computers execute software routines which enable, for example, the seven layers of the OSI model of computer networking or equivalent in a wireless phone network. Network 2450 may provide communication services to Site 100 and components thereof. Network 2450 may be accessed wirelessly and/or via wireline connections through, for example, a pivot arm of Site 100.

Figure 25:
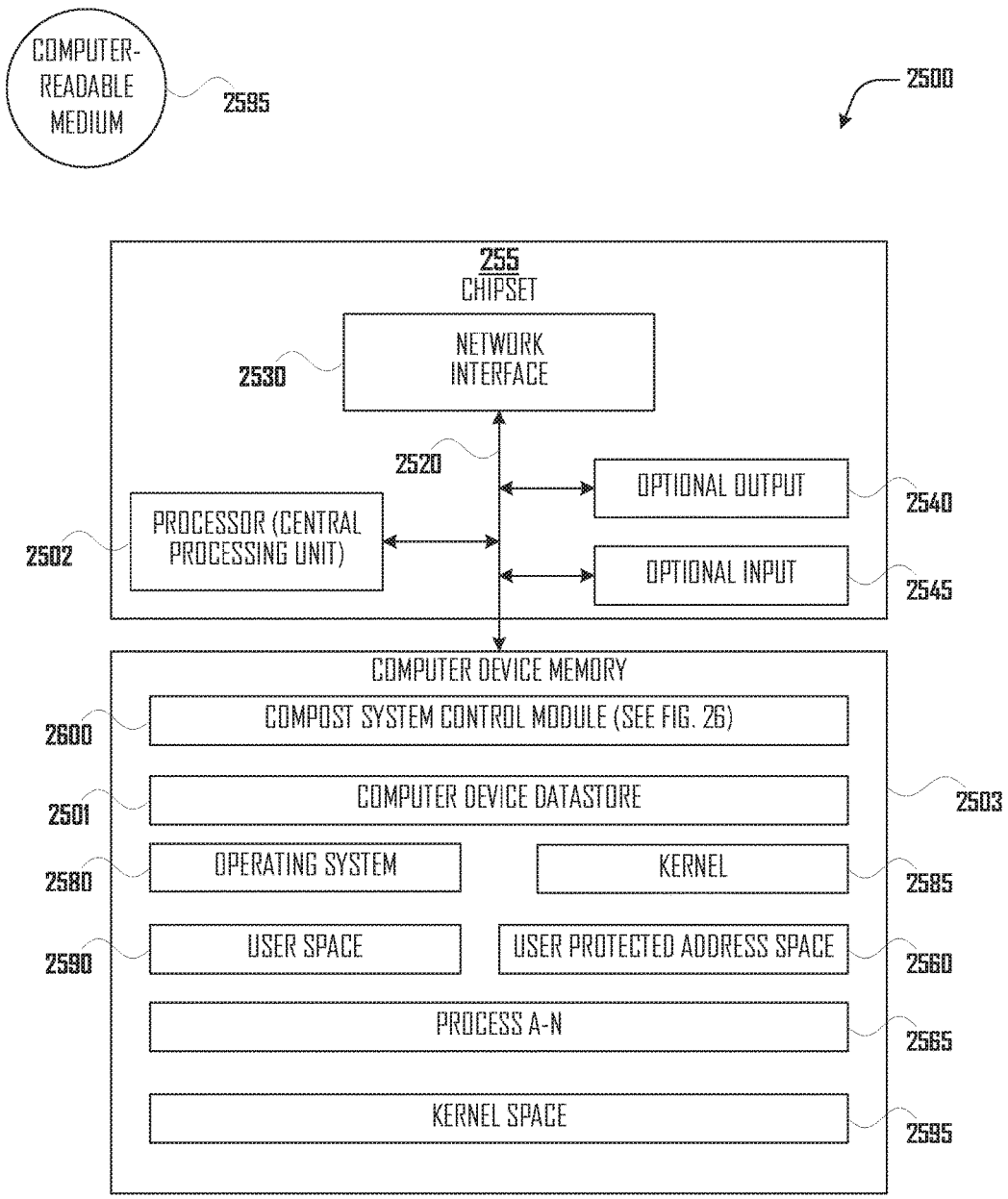
FIG. 25 is a functional block diagram illustrating an example of an embodiment of the computer device of FIG. 24.

FIG. 25 is a functional block diagram illustrating an example of computer device 2500 incorporated with the teachings of the present disclosure, according to some embodiments. Computer device 2500 may include chipset 2555, comprising processor 2502, input/output (I/O) port(s) and peripheral device interfaces, such as output interface 2540 and input interface 2545, and network interface 2530, and computer device memory 2503, all interconnected via bus 2520. Network Interface 2530 may be utilized to couple processor 2502 to a network interface card (NIC) to form connections with network 2450, with computer device datastore 2501, or to form device-to-device connections with other computers.

Chipset 2555 may include communication components and/or paths, e.g., buses 2520, that couple processor 2502 to peripheral devices, such as, for example, output interface 2540 and input interface 2545, which may be connected via I/O ports. For example, chipset 2555 may include a peripheral controller hub (PCH) (not shown). In another example, chipset 2555 may include a sensors hub, such as to receive information from sensors of or in Site 100. Input interface 2545 and output interface 2540 may couple processor 2502 to input and/or output devices that include, for example, user and machine interface device(s) including a display, a touchscreen display, printer, keypad, keyboard, etc., sensor(s) including thermometers, position and index sensors, inertial measurement units, cameras, global positioning system (GPS), other sensors of or in the compost handling equipment, pivot arm, air handling system, and water collection system, storage device(s) including hard disk drives, solid-state drives, removable storage media, etc. I/O ports for input interface 2545 and output interface 2540 may be configured to transmit and/or receive commands and/or data according to one or more communications protocols. For example, one or more of the I/O ports may comply and/or be compatible with a universal serial bus (USB) protocol, peripheral component interconnect (PCI) protocol (e.g., PCI express (PCIe)), or the like.

Computer device memory 2503 may generally comprise a random access memory ("RAM"), a read only memory ("ROM"), and a permanent mass storage device, such as a disk drive or SDRAM (synchronous dynamic random-access memory). Computer device memory 2503 may store program code for software modules or routines, such as, for example, compost system control module 2600 (illustrated and discussed further in relation to FIG. 26).

Computer device memory 2503 may also store operating system 2580. These software components may be loaded from a non-transient computer readable storage medium 2595 into computer device memory 2503 using a drive mechanism associated with a non-transient computer readable storage medium 2595, such as a floppy disc, tape, DVD/CD-ROM drive, memory card, or other like storage medium. In some embodiments, software components may also or instead be loaded via a mechanism other than a drive mechanism and computer readable storage medium 2595 (e.g., via network interface 2530).

Computer device memory 2503 is also illustrated as comprising kernel 2585, kernel space 2595, user space 2590, user protected address space 2560, and computer device datastore 2501.

Computer device memory 2503 may store one or more process 2565 (i.e., executing software application(s)). Process 2565 may be stored in user space 2590. Process 2565 may include one or more other process 2565a . . . 2565n. One or more process 2565 may execute generally in parallel, i.e., as a plurality of processes and/or a plurality of threads.

Computer device memory 2503 is further illustrated as storing operating system 2580 and/or kernel 2585. The operating system 2580 and/or kernel 2585 may be stored in kernel space 2595. In some embodiments, operating system 2580 may include kernel 2585. One or more process 2565a . . . 2565n may be unable to directly access kernel space 2595. In other words, operating system 2580 and/or kernel 2585 may attempt to protect kernel space 2595 and prevent access by one or more of process 2565a . . . 2565n.

Kernel 2585 may be configured to provide an interface between user processes and circuitry associated with computer device 2500. In other words, kernel 2585 may be configured to manage access to processor 2502, chipset 2555, I/O ports and peripheral devices by process 2565. Kernel 2585 may include one or more drivers configured to manage and/or communicate with elements of computer device 2500 (i.e., processor 2502, chipset 2555, I/O ports and peripheral devices).

Computer device datastore 2501 of FIG. 24 may comprise multiple datastores, in and/or remote with respect to computer device 2500. Datastore 2501 may be distributed. The components of computer device datastore 2501 may include data groups used by modules and/or routines. The data groups used by modules or routines may be represented by a cell in a column or a value separated from other values in a defined structure in a digital document or file. Though referred to herein as individual records or entries, the records may comprise more than one database entry. The database entries may be, represent, or encode numbers, numerical operators, binary values, logical values, text, string operators, references to other database entries, joins, conditional logic, tests, and similar.

Figure 26:
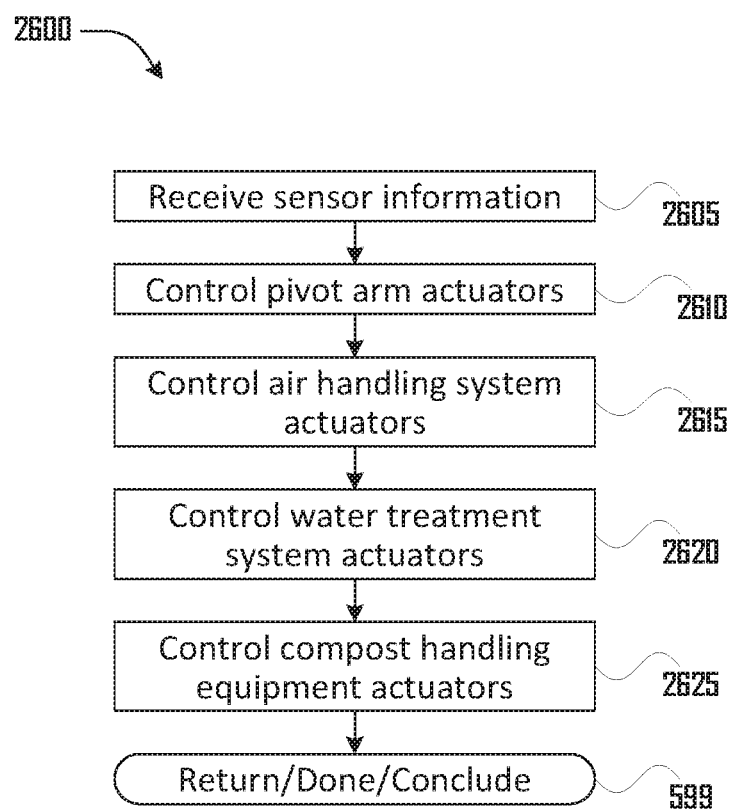
FIG. 26 is a flow chart illustrating an example of the compost system control module.

FIG. 26 is a flow diagram illustrating an example of a method for a compost system control module 2600, according to some embodiments. Compost system control module 2600 may be executed by, for example, computer device 2500. The blocks of compost system control module 2600 may be performed in a different order, other than as illustrated in FIG. 26.

At block 2605, sensor information may be received from, for example, sensors of or in Site 100. Such sensors may include, for example, position sensors to detect a position of components such as the pivot arm, conveyor belts, carriages secured to compost handling equipment, compost handling equipment, depth sensors to detect a depth of bulk material on the aerated pad, moisture sensors, temperature sensors, operational status sensors, water level sensors, BOD sensors, methane, VOC, or odor sensors, rainfall sensors, pressure sensors, airflow sensors, magnetic sensors, loading rate sensors, and the like.

At block 2610, compost system control module 2600 may control pivot arm actuators in response to input, such as input from received sensor information. Pivot arm actuators may include, for example, ground drive systems, conveyor belt actuators, convey belt extension actuators, valves, sprinklers, air knife vacuum heads, and the like. Control of such actuators may be to deposit bulk material and/or a biocover on an aeration pad, to move bulk material on the aeration pad, to move bulk material toward the center of aeration pad as the bulk material ages, to maintain a moisture level in the bulk material, to maintain a temperature in the bulk material. Control of such actuators may involve feedback with sensor information, such as to control an actuator until a desired sensor result is achieved or a passage of time occurs. For example, the pivot arm actuators may be controlled to deposit a desired depth and/or pattern of bulk material on the aeration pad, as may be determined according to sensor input. For example, sprinklers may be opened for a period of time and/or until a target moisture content is achieved in bulk material.

At block 2615, compost system control module 2600 may control air handling system actuators in response to input, such as input from received sensor information. Air handling system actuators may include, for example, blowers, air pressurization systems, valves, purge and cleanout systems, air conditioning and heating units, humidifiers, duct louvers, air filters, and the like. Control of such actuators may be to control a temperature, humidity, dust level, methane or odor level, and/or pressure of a volume of air, wherein the volume of air may be in a duct of the air handling system, in a water containment vessel, in bulk material, above bulk material. Control of such actuators may be to clear nozzles. For example, during turning operations or during other circumstances which may result in plugging of nozzles, high velocity airflow, such as between 50 and 100 miles per hour at the nozzle, may be provided. At other times, such as to aerate bulk material, nozzle velocity of between 5 and 50 miles per hour may be provided. Control of air handling system actuators may involve feedback with sensor information, such as to control air handling system actuators until a sensor information is received, such as a temperature in the bulk material, or the like.

At block 2620, compost system control module 2600 may control water collection system actuators in response to input, such as input from received sensor information. Water collection system actuators may include, for example, valves, and actuators of the air handling system. Control of such actuators may be to control a temperature, a BOD of a volume of water, wherein the volume of water may be in a water containment vessel. Control of such actuators may be to clear nozzles. Control of the water collection system actuators may involve feedback with sensor information, such as to control valves and actuators of the air handling system to bubble air through a water containment vessel until a desired BOD is achieved.

At block 2625, compost system control module 2600 may control compost handling equipment actuators in response to input, such as input from received sensor information. Compost handling equipment actuators may include, for example, a mobile compost turner, a grinder, a loader, and/or a screener. Control of such actuators may be to turn over bulk material, to turn over bulk material toward a center of Site 100, to move bulk material into a screener or onto a conveyor belt, to grind bulk material, to move bulk material, or the like. Control of compost handling equipment actuators may involve feedback with sensor information, such as to move bulk material from an area of Site 100 until the depth of bulk material in the area is reduced to the surface of the aerated pad.

Following are examples of the disclosed compost system:

Example 1

A system for composting comprising: an aerated pad to receive a bulk material to be composted into a compost product, wherein the aerated pad comprises an air nozzle and a drain to direct water from the bulk material to a water collection system; a pivot arm attached to a center of the aerated pad, wherein the pivot arm is to at least one of deposit the bulk material on the aerated pad or provide a utility to the system for composting; and a control module to manage a temperature inside the bulk material using the air nozzle.

Example 2

The system according to at least one of Example 1 or any other Example herein, wherein the utility comprises at least one of i) a water supply, ii) a power supply, iii) a data connection, or iv) a positive or negative pressure air duct.

Example 3

The system according to at least one of Example 1 or any other Example herein, wherein the air nozzle is below grade.

Example 4

The system according to at least one of Example 3 or any other Example herein, wherein the air nozzle comprise a first pipe section attached to a main air manifold, a second pipe sized to fit around or inside of the first pipe, an air orifice to fit inside of the second pipe, and a variable spacer to position the air orifice at a height relative to a surface of the aerated pad.

Example 5

The system according to at least one of Example 4 or any other Example herein, wherein the air nozzle further comprises a securement fixture to secure the first and second pipes in a relative position when the aerated pad is poured.

Example 6

The system according to at least one of Example 4 or any other Example herein, wherein the variable spacer comprises a variable spacer portion which may be removed as the surface of the aerated pad wears over time.

Example 7

The system according to at least one of Example 1 or any other Example herein, further comprising an air pressurization system to provide positive or negative air pressure to the air nozzle.

Example 8

The system according to at least one of Example 7 or any other Example herein, wherein the control module is to direct the air pressurization system to provide positive or negative air pressure to the air nozzle in response to one or more of a temperature inside the bulk material, a temperature of air in the air pressurization system, a temperature of air above the bulk material, a biologic activity of the bulk material, an oxygen level in the bulk material, an age of a portion of the bulk material, or a moisture content of at least one of the bulk material or a volume of air in the air pressurization system.

Example 9

The system according to at least one of Example 1 or any other Example herein, further comprising an air handling system, wherein the air handling system is to at least one of i) treat a volume of air for odors, ii) increase or decrease a temperature of the volume of air, iii) increase or decrease a level of moisture in the volume of air, iv) reduce a dust level in the volume of air, or iv) increase or decrease a temperature of at least a portion of the bulk material.

Example 10

The system according to at least one of Example 9 or any other Example herein, wherein the air handling system is to collect the volume of air from at least one of i) a location proximate to active deposition of the bulk material on the aerated pad, ii) a location proximate to active turning over of the bulk material, iii) a water catchment vessel, or iv) the air nozzle.

Example 11

The system according to at least one of Example 9 or any other Example herein, wherein to increase or decrease the temperature of the volume of air, the air handling system is to transport a heat energy between the volume of air and a heat sink or heat source.

Example 12

The system according to at least one of Example 11 or any other Example herein, wherein to transport the heat energy between the volume of air and the heat sink or heat source, the air handling system comprises a thermal contact between the volume of air and the heat sink or heat source and wherein the heat sink or heat source comprises at least one of i) the aerated pad, ii) a ground beneath the aerated pad, or iii) a volume of water.

Example 13

The system according to at least one of Example 12 or any other Example herein, wherein the thermal contact between the volume of air and the heat sink or heat source comprises at least one of i) an air duct to contain the volume of air, ii) a water channel around an exterior of the air duct, ii) a water injector to inject the volume of the water into the volume of air, or iii) an air injector to inject the volume of air into the volume of water.

Example 14

The system according to at least one of Example 12 or any other Example herein, wherein the volume of water is of a water collection system.

Example 15

The system according to at least one of Example 9 or any other Example herein, wherein the air handling system comprises at least one of i) a flushing system to flush at least one of a solid or a liquid from the air handling system or ii) an air filter.

Example 16

The system according to at least one of Example 15 or any other Example herein, wherein the air filter comprises at least one of i) a porous solid media with a high surface area, wherein the high surface area is to contact the volume of air, ii) a volume of water, wherein the volume of air is to be bubbled through the volume of water, or iii) a cyclotron separator.

Example 17

The system according to at least one of Example 1 or any other Example herein, further comprising the water collection system and wherein the water collection system is to at least one of i) reduce a Biochemical Oxygen Demand (BOD) of a volume of water, ii) transport a heat energy into or out of the volume of water, or iii) apply the volume of water to the bulk material.

Example 18

The system according to at least one of Example 17 or any other Example herein, wherein the water collection system comprises at least one of i) a peripheral catchment vessel or ii) a central catchment vessel.

Example 19

The system according to at least one of Example 18 or any other Example herein, wherein the bulk material is deposited in a circular shape around a center of the pivot arm, wherein a rectangular perimeter surrounds the circular shape, and wherein the peripheral catchment vessel is in a corner of the rectangular perimeter.

Example 20

The system according to at least one of Example 18 or any other Example herein, wherein the water collection system comprises both the peripheral catchment vessel and the central catchment vessel and wherein the peripheral catchment vessel is to feed water to the central catchment vessel.

Example 21

The system according to at least one of Example 18 or any other Example herein, wherein at least one of the peripheral catchment vessel or the central catchment vessel comprises a floating dock and an air plenum below the floating dock.

Example 22

The system according to at least one of Example 21 or any other Example herein, wherein the floating dock comprises an air filter, wherein the air filter is to filter a volume of air released under positive pressure beneath the floating dock.

Example 23

The system according to at least one of Example 22 or any other Example herein, wherein the volume of air released under positive pressure beneath the floating dock is released below a water line.

Example 24

The system according to at least one of Example 22 or any other Example herein, wherein the filter comprises porous solid media with a high surface area on top of the floating dock, wherein the high surface area is to contact a volume of air.

Example 25

The system according to at least one of Example 17 or any other Example herein, wherein the water collection system is to reduce the BOD in the volume of water to a level at which the volume of water can be applied to the bulk material.

Example 26

The system according to at least one of Example 17 or any other Example herein, wherein the water collection system is to bubble a volume of air into the volume of water.

Example 27

The system according to at least one of Example 1 or any other Example herein, wherein the aerated pad comprises a slope.

Example 28

The system according to at least one of Example 27 or any other Example herein, wherein the slope is at least one of i) outward, and wherein the system for composting further comprises a channel to direct a flow of water toward a peripheral catchment vessel or ii) inward, and wherein the system for composting further comprises a channel to direct a flow of water toward a central catchment vessel.

Example 29

The system according to at least one of Example 1 or any other Example herein, wherein the pivot arm rotates about the center of the aerated pad and wherein the pivot arm comprises at least one of i) a conveyor belt to convey the bulk material from a bulk material receiving area onto an area of the aerated pad, ii) a water outlet to apply a volume of water to the bulk material, iii) an air knife and/or air vacuum directed to the bulk material to be deposited by the pivot arm, wherein the air knife and/or air vacuum is to remove a low density item from the bulk material, iv) a rotary bulk material flail, v) a downtube, wherein the downtube is to direct the bulk material onto the aerated pad, vi) a watering downtube, wherein the watering downtube is to direct the bulk material onto the aerated pad and is to release water into the bulk material in the downtube, vii) a position sensor, viii) a depth sensor, wherein the depth sensor is to measure a depth of bulk material on the aerated pad, ix) a temperature sensor, wherein the temperature sensor is to measure a temperature of the bulk material, x) an extendable section, or xi) a carriage, wherein the carriage is to be secured to a compost handling equipment.

Example 30

The system according to at least one of Example 29 or any other Example herein, wherein the compost handling equipment comprises at least one of i) a mobile compost turner, wherein the mobile compost turner is to turn over the bulk material on the aerated pad, ii) a grinder, wherein the grinder is to grind the bulk material, or iii) a screener, wherein the screener is to screen the bulk material.

Example 31

The system according to at least one of Example 30 or any other Example herein, wherein the mobile compost turner is further to transport the bulk material toward the center of the aerated pad as it is to turn over the bulk material on the aerated pad.

Example 32

The system according to at least one of Example 31 or any other Example herein, wherein the control module is to operate the mobile compost turner to transport the bulk material toward the center of the aerated pad as the bulk material ages and reduces in volume.

Example 33

The system according to at least one of Example 30 or any other Example herein, wherein the mobile compost turner is further to rotate around the center of the aerated pad while it is to turn over the bulk material on the aerated pad in concentric windrows, relative to the center of the aerated pad.

Example 34

The system according to at least one of Example 33 or any other Example herein, wherein as the mobile compost turner is to turn over the bulk material on the aerated pad in concentric windrows, it is to transport the bulk material toward the center of the aerated pad.

Example 35

The system according to at least one of Example 30 or any other Example herein, wherein the compost turner is further to turn over the bulk material on the aerated pad in axial windrow sections.

Example 36

The system according to at least one of Example 29 or any other Example herein, wherein the carriage is mobile along the pivot arm.

Example 37

The system according to at least one of Example 30 or any other Example herein, wherein the screener is to provide a screen product of the screener to the pivot arm, wherein the pivot arm is to deposit the screen product on at least one of i) the bulk material, or ii) a waste receptacle.

The invention claimed is:

1. A system for composting comprising:
    a circular aerated concrete pad to support a bulk material to be composted into a compost product, wherein the circular aerated concrete pad comprises an air nozzle below grade of the aerated concrete pad and a drain to direct water from the bulk material to a water collection system;
    an arc of bulk material on the circular aerated concrete pad, wherein the arc of bulk material comprises more than 180 degrees and wherein the arc of bulk material surrounds a center area of the circular aerated concrete pad and wherein a keyway provides an access way clear of bulk material to and from the center area;
    a mobile compost turner to transport a windrow of bulk material of the arc of bulk material toward the center area of the aerated concrete pad as the bulk material ages and reduces in volume, wherein a reduction in area of the circular aerated concrete pad is consistent with a rate of reduction of the bulk material as it ages and reduces in volume; and
    a control module to manage a temperature inside the bulk material using the air nozzle.

2. The system according to claim 1, wherein the air nozzle comprises a first pipe section attached to a main air manifold, a second pipe sized to fit around or inside of the first pipe, an air orifice to fit inside of the second pipe, and a variable spacer to position the air orifice at a height relative to a surface of the circular aerated concrete pad.

3. The system according to claim 2, wherein the air nozzle further comprises a securement fixture to secure the first and second pipes in a relative position when the circular aerated concrete pad is poured.

4. The system according to claim 2, wherein the variable spacer comprises a variable spacer portion which may be removed as the surface of the circular aerated concrete pad wears over time.

5. The system according to claim 1, further comprising an air pressurization system to provide positive or negative air pressure to the air nozzle.

6. The system according to claim 5, wherein the control module is to direct the air pressurization system to provide positive or negative air pressure to the air nozzle in response to a temperature inside the bulk material and in response to one or more of a temperature of air in the air pressurization system, a temperature of air above the bulk material, a biologic activity of the bulk material, an oxygen level in the bulk material, an age of a portion of the bulk material, a moisture content of at least one of the bulk material, or a volume of air in the air pressurization system.

7. The system according to claim 1, further comprising an air handling system, wherein control module is to manage the air handling system to manage temperature inside the bulk material using the air nozzle to increase or decrease a temperature of at least a portion of the bulk material and is also to at least one of treat a volume of air for odors, increase or decrease a temperature of the volume of air, increase or decrease a level of moisture in the volume of air, or reduce a dust level in the volume of air, or.

8. The system according to claim 7, wherein the air handling system is to collect the volume of air from the air nozzle and at least one of a location proximate to active deposition of the bulk material on the circular aerated concrete pad, a location proximate to active turning over of the bulk material, and a water catchment vessel.

9. The system according to claim 7, wherein to increase or decrease the temperature of the volume of air, the control module is to manage the air handling system to transport a heat energy between the volume of air and a heat sink or heat source, wherein to transport the heat energy between the volume of air and the heat sink or heat source, the air handling system comprises a thermal contact between the volume of air and the heat sink or heat source and wherein the heat sink or heat source comprises at least one of the circular aerated concrete pad, a ground beneath the circular aerated concrete pad, or a volume of water and wherein the thermal contact between the volume of air and the heat sink or heat source comprises at least one of an air duct to contain the volume of air, a water channel around an exterior of the air duct, a water injector to inject the volume of the water into the volume of air, or an air injector to inject the volume of air into the volume of water.

10. The system according to claim 9, wherein the volume of water is of a water collection system.

11. The system according to claim 7, wherein the air handling system comprises at least one of a flushing system to flush at least one of a solid or a liquid from the air handling system or an air filter.

12. The system according to claim 11, wherein the air filter comprises at least one of a porous solid media with a high surface area, wherein the high surface area is to contact the volume of air, a volume of water, wherein the volume of air is to be bubbled through the volume of water, or a cyclotron separator.

13. The system according to claim 1, wherein the water collection system is to at least one of reduce a Biochemical Oxygen Demand (BOD) of a volume of water, transport a heat energy into or out of the volume of water, or apply the volume of water to the bulk material.

14. The system according to claim 13, wherein the water collection system comprises at least one of a peripheral catchment vessel or a central catchment vessel.

15. The system according to claim 14, wherein a rectangular perimeter surrounds the circular aerated concrete pad, and wherein the peripheral catchment vessel is in a corner of the rectangular perimeter.

16. The system according to claim 14, wherein the water collection system comprises both the peripheral catchment vessel and the central catchment vessel and wherein the peripheral catchment vessel is to feed water to the central catchment vessel.

17. The system according to claim 14, wherein at least one of the peripheral catchment vessel or the central catchment vessel comprises a floating dock and an air plenum below the floating dock, wherein the floating dock comprises an air filter, wherein the air filter is to filter a volume of air released under positive pressure beneath the floating dock.

18. The system according to claim 17, wherein the filter comprises porous solid media with a high surface area on top of the floating dock, wherein the high surface area is to contact a volume of air.

19. The system according to claim 1, further comprising a pivot arm attached to a center of the circular aerated pad; wherein the pivot arm rotates about the center of the circular aerated pad; wherein the pivot arm comprises a carriage, wherein the carriage is mobile along the pivot arm, wherein the carriage is secured to a compost handling equipment, wherein the compost handling equipment comprises the mobile compost turner.

20. The system according to claim 19, wherein the compost handling equipment further comprises at least one of a grinder, wherein the grinder is to grind the bulk material, or a screener, wherein the screener is to screen the bulk material.

21. The system according to claim 19, wherein the pivot arm further comprises at least one of a water outlet to apply a volume of water to the bulk material, an air knife and/or air vacuum directed to the bulk material to be deposited by the pivot arm, wherein the air knife and/or air vacuum is to remove a low density item from the bulk material, a rotary bulk material flail, a downtube, wherein the downtube is to direct bulk material from the conveyor belt onto the circular aerated concrete pad, a watering downtube, wherein the watering downtube is to direct the bulk material onto the aerated pad and is to release water into the bulk material in the downtube, a position sensor, a depth sensor, wherein the depth sensor is to measure a depth of bulk material on the circular aerated concrete pad, a temperature sensor, wherein the temperature sensor is to measure a temperature of the bulk material, or an extendable section of the pivot arm.

22. The system according to claim 1, wherein the windrow is a concentric windrow.

23. The system according to claim 1, wherein the windrow is an axial windrow.

24. The system according to claim 19, wherein the pivot arm further comprises a conveyor belt to convey the bulk material from a bulk material receiving area to form the arc of bulk material.

25. The system according to claim 24, wherein the pivot arm further provides a utility to the system for composting, wherein the utility comprises at least one of a water supply, a power supply, a data connection, or a positive or negative pressure air duct.

26. The System according to claim 1, wherein the control module is further to operate the mobile compost turner to transport the bulk material toward the center of the aerated concrete pad as the bulk material ages and reduces in volume.

* * * * *